United States Patent
Swayze et al.

(10) Patent No.: US 10,492,789 B2
(45) Date of Patent: Dec. 3, 2019

(54) POWERED SURGICAL CIRCULAR STAPLER WITH REMOVABLE CARTRIDGE AND CONCENTRIC ROTARY DRIVE SHAFTS

(71) Applicant: Ethicon Endo-Surgery, LLC, Guaynabo, PR (US)

(72) Inventors: Jeffrey S. Swayze, West Chester, OH (US); Chester O. Baxter, III, Loveland, OH (US); Frederick E. Shelton, IV, Hillsboro, OH (US); Gregory W. Johnson, Milford, OH (US)

(73) Assignee: Ethicon LLC, Guaynabo, PR (US)

( * ) Notice: Subject to any disclaimer, the term of this patent is extended or adjusted under 35 U.S.C. 154(b) by 292 days.

(21) Appl. No.: 15/268,740

(22) Filed: Sep. 19, 2016

(65) Prior Publication Data

US 2017/0000492 A1   Jan. 5, 2017

Related U.S. Application Data

(63) Continuation of application No. 13/716,313, filed on Dec. 17, 2012, now Pat. No. 9,532,783.

(51) Int. Cl.
*A61B 17/115* (2006.01)
*A61B 17/00* (2006.01)
*A61B 90/00* (2016.01)

(52) U.S. Cl.
CPC ........ *A61B 17/115* (2013.01); *A61B 17/1155* (2013.01); *A61B 2017/00017* (2013.01);
(Continued)

(58) Field of Classification Search
CPC ..... A61B 17/10; A61B 17/105; A61B 17/068; A61B 17/115
(Continued)

(56) References Cited

U.S. PATENT DOCUMENTS 4,606,343 A   8/1986 Conta et al.
4,805,823 A   2/1989 Rothfuss
(Continued)

FOREIGN PATENT DOCUMENTS

EP   1 813 211   8/2007
EP   1 982 657   10/2008
(Continued)

OTHER PUBLICATIONS

International Search Report and Written Opinion dated Jul. 4, 2014 re Application No. PCT/US13/75242.
(Continued)

*Primary Examiner* — Nathaniel C Chukwurah
(74) *Attorney, Agent, or Firm* — Frost Brown Todd LLC

(57) ABSTRACT

A surgical instrument includes a stapling head assembly with at least a portion of the stapling head assembly configured to removably couple with a portion of a shaft assembly. The stapling head assembly has a cartridge housing, a staple deck, a plurality of staples, a staple driver, a cylindraceous knife, a trocar, and first and second drive members that are coaxial with a longitudinal axis. The first and second drive members are configured to receive a rotatable drive element thereagainst. The first drive member drives translation of at least one of the staple driver, the cylindraceous knife, or the trocar. The second drive member drives translation of a remaining of at least one of the staple driver, the cylindraceous knife, or the trocar. The second drive member is positioned radially inwardly from the first drive member.

20 Claims, 34 Drawing Sheets

(52) U.S. Cl.
CPC ............... *A61B 2017/00115* (2013.01); *A61B 2017/00393* (2013.01); *A61B 2017/00398* (2013.01); *A61B 2017/00734* (2013.01); *A61B 2090/0811* (2016.02)

(58) Field of Classification Search
USPC .......... 227/4, 19, 176.1, 180.1, 178.1, 179.1
See application file for complete search history.

(56) References Cited

U.S. PATENT DOCUMENTS

| | | | |
|---|---|---|---|
| 4,893,622 A | 1/1990 | Green et al. | |
| 4,903,697 A | 2/1990 | Resnick et al. | |
| 5,205,459 A | 4/1993 | Brinkerhoff et al. | |
| 5,271,544 A | 12/1993 | Fox et al. | |
| 5,275,322 A | 1/1994 | Brinkerhoff et al. | |
| 5,285,945 A | 2/1994 | Brinkerhoff et al. | |
| 5,292,053 A | 3/1994 | Bilotti et al. | |
| 5,333,773 A | 8/1994 | Main et al. | |
| 5,350,104 A | 9/1994 | Main et al. | |
| 5,415,334 A | 5/1995 | Williamson, IV et al. | |
| 5,465,895 A | 11/1995 | Knodel et al. | |
| 5,533,661 A | 7/1996 | Main et al. | |
| 5,597,107 A | 1/1997 | Knodel et al. | |
| 5,632,432 A | 5/1997 | Schulze et al. | |
| 5,673,840 A | 10/1997 | Schulze et al. | |
| 5,704,534 A | 1/1998 | Huitema et al. | |
| 5,814,055 A | 9/1998 | Knodel et al. | |
| 6,783,524 B2 | 8/2004 | Anderson et al. | |
| 6,978,921 B2 | 12/2005 | Shelton, IV et al. | |
| 6,978,922 B2 | 12/2005 | Bilotti et al. | |
| 7,000,818 B2 | 2/2006 | Shelton, IV et al. | |
| 7,143,923 B2 | 12/2006 | Shelton, IV et al. | |
| 7,303,108 B2 | 12/2007 | Shelton, IV | |
| 7,367,485 B2 | 5/2008 | Shelton, IV et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,434,715 B2 | 10/2008 | Shelton, IV et al. | |
| 7,494,038 B2 | 2/2009 | Milliman | |
| 7,721,930 B2 | 5/2010 | McKenna et al. | |
| 7,794,475 B2 | 9/2010 | Hess et al. | |
| 7,959,050 B2 | 6/2011 | Smith et al. | |
| 7,963,433 B2 | 6/2011 | Whitman et al. | |
| 8,028,885 B2 | 10/2011 | Smith et al. | |
| 8,286,845 B2 | 10/2012 | Perry et al. | |
| 8,286,846 B2 | 10/2012 | Smith et al. | |
| 8,413,870 B2 | 4/2013 | Pastorelli et al. | |
| 8,573,459 B2 | 11/2013 | Smith et al. | |
| 8,585,714 B2 | 11/2013 | Weisel et al. | |
| 8,627,995 B2 | 1/2014 | Smith et al. | |
| 8,640,940 B2 | 2/2014 | Ohdaira | |
| 8,752,749 B2 | 6/2014 | Moore et al. | |
| 9,113,884 B2 | 8/2015 | Shelton et al. | |
| 9,289,207 B2 | 3/2016 | Shelton | |
| 9,445,816 B2 | 9/2016 | Swayze et al. | |
| 9,463,022 B2 | 10/2016 | Swayze et al. | |
| 9,498,222 B2 | 11/2016 | Scheib et al. | |
| 9,532,783 B2 | 1/2017 | Swayze et al. | |
| 9,681,873 B2 | 6/2017 | Smith et al. | |
| 2005/0187576 A1* | 8/2005 | Whitman ............. A61B 17/115 606/219 |
| 2007/0270784 A1* | 11/2007 | Smith ................. A61B 17/1114 606/1 |
| 2008/0255413 A1 | 10/2008 | Zemlok et al. | |
| 2011/0022032 A1 | 1/2011 | Zemlok et al. | |
| 2011/0125138 A1 | 5/2011 | Malinouskas et al. | |
| 2014/0000411 A1 | 1/2014 | Shelton, IV et al. | |
| 2014/0151429 A1 | 6/2014 | Scheib et al. | |
| 2014/0151430 A1 | 6/2014 | Scheib et al. | |
| 2014/0158747 A1 | 6/2014 | Measamer et al. | |
| 2014/0166728 A1 | 6/2014 | Swayze et al. | |
| 2016/0192939 A1 | 7/2016 | Sgroi et al. | |
| 2017/0000488 A1 | 1/2017 | Swayze et al. | |
| 2017/0000489 A1 | 1/2017 | Swayze et al. | |
| 2017/0000490 A1 | 1/2017 | Swayze et al. | |
| 2017/0000491 A1 | 1/2017 | Swayze et al. | |

FOREIGN PATENT DOCUMENTS

| | | |
|---|---|---|
| EP | 2 044 888 | 4/2009 |
| EP | 2 491 872 | 5/2009 |
| EP | 2 316 345 A1 | 5/2011 |
| JP | 2009-106752 A | 5/2009 |
| WO | WO 2016/057225 | 4/2016 |

OTHER PUBLICATIONS

International Preliminary Report on Patentability dated Jun. 23, 2015 re Application No. PCT/US13/75242.
U.S. Appl. No. 15/268,694.
U.S. Appl. No. 15/268,705.
U.S. Appl. No. 15/268,709.
U.S. Appl. No. 15/268,724.
Chinese Office Action, Notification of the First Office Action, and Search Report dated Jan. 25, 2017 for Application No. CN 20130066186.4, 8 pgs.
Chinese Office Action, The Second Office Action, dated Jun. 14, 2017 for Application No. CN 201380066186.4, 7 pgs.
European Examination Report dated May 3, 2017 for Application No. EP 13821022.4, 4 pgs.
Japanese Office Action, Notice of Reasons for Refusal, and Search Report by Registered Searching Authority, dated Aug. 1, 2017 for Application No. JP 2015-548030, 25 pgs.
Japanese Office Action, Decision of Refusal, dated Jan. 9, 2018 for Application No. JP 2015-548030, 2 pgs.
Japanese Office Action, Decision to Grant a Patent, dated Jul. 31, 2018 for Application No. JP 2015-548030, 2 pgs.
Mexican Office Action dated Mar. 13, 2018 for Application No. MX/a/2015/007739, 2 pgs.
Russian Office Action dated Nov. 3, 2017 for Application No. RU 2015129083/14, 4 pgs.

* cited by examiner

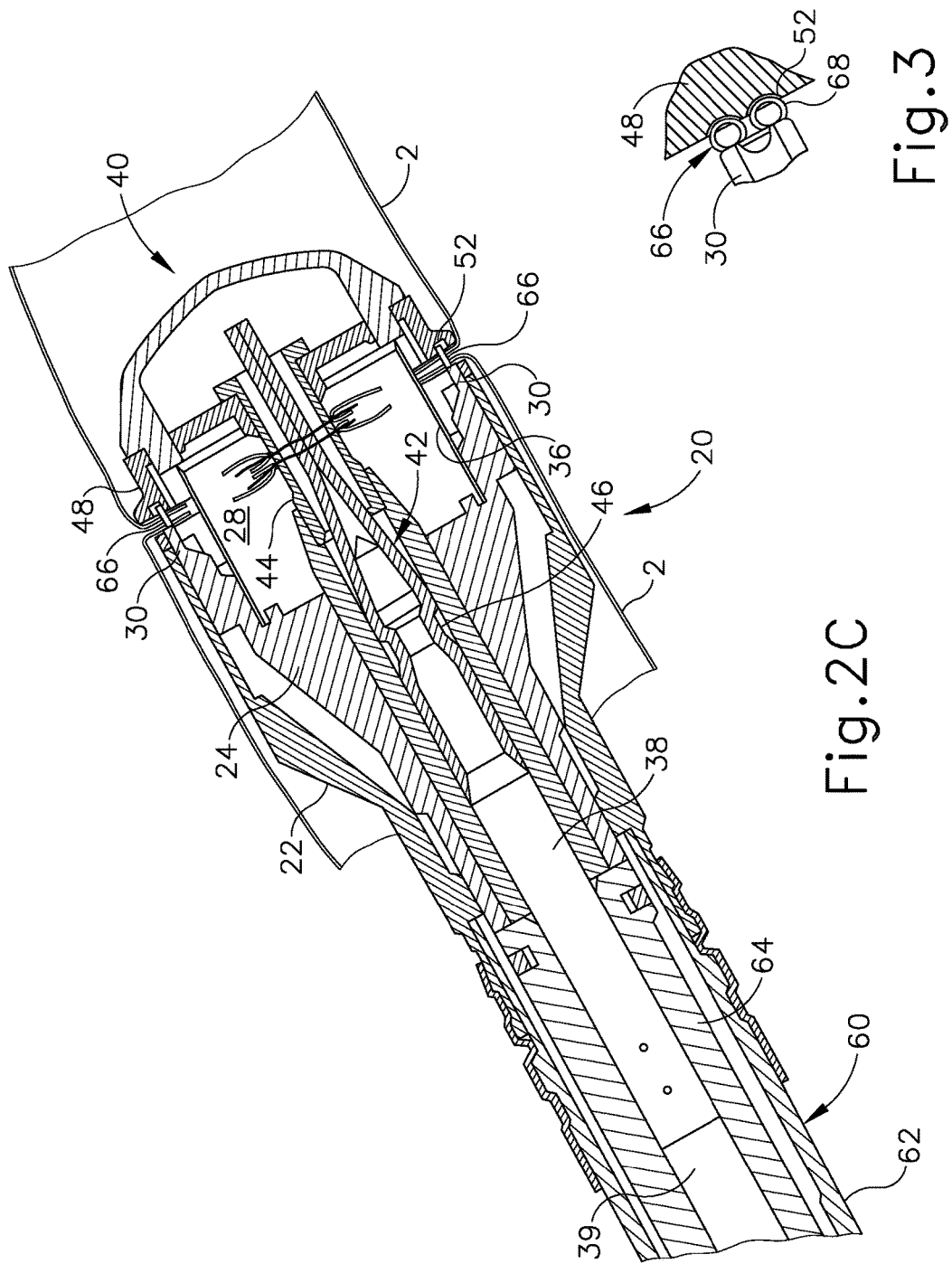

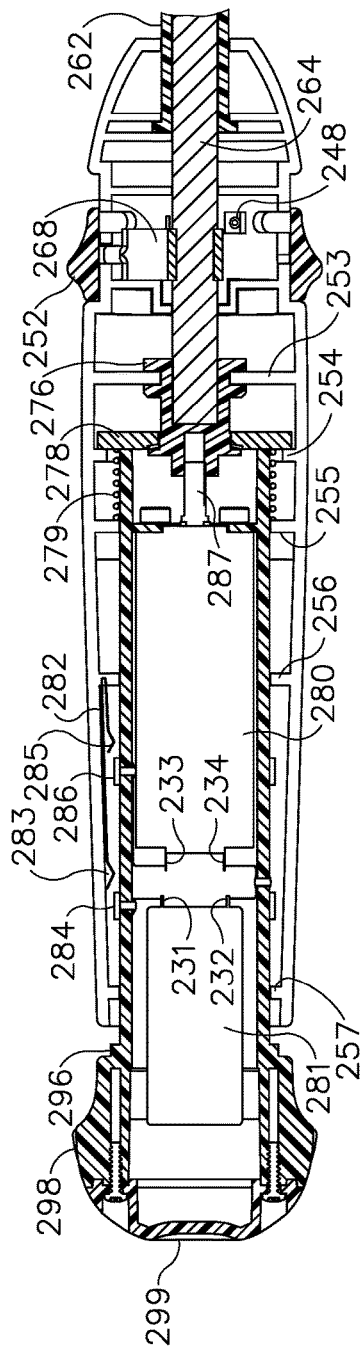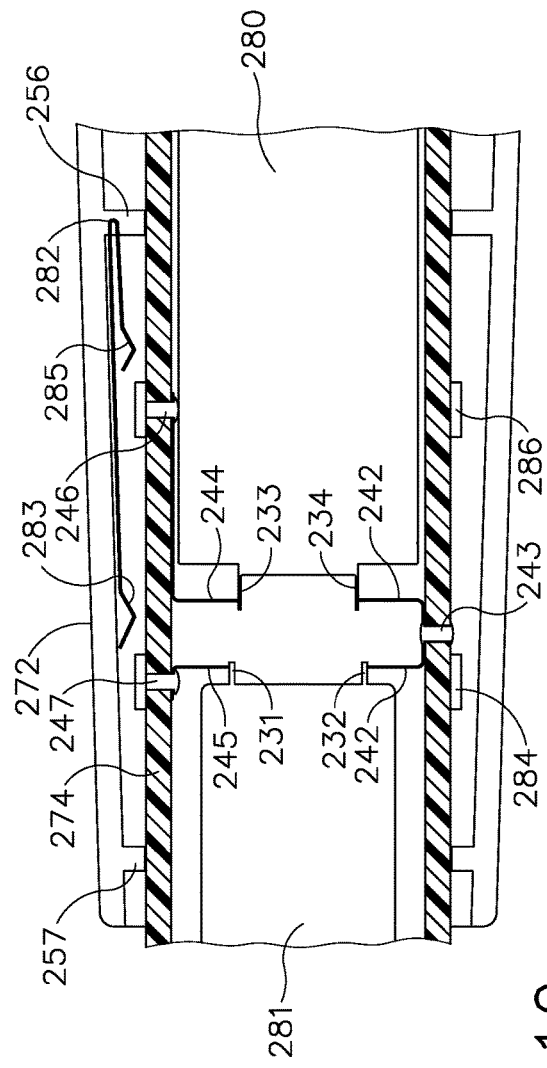

NEW SHEET

POWERED SURGICAL CIRCULAR STAPLER WITH REMOVABLE CARTRIDGE AND CONCENTRIC ROTARY DRIVE SHAFTS

This application is a continuation of U.S. Non-Provisional application Ser. No. 13/716,313, filed Dec. 17, 2012, entitled "Circular Stapler with Selectable Motorized and Manual Control, Including a Control Ring," published as U.S. Pub. No. 2014/0166717 on Jun. 19, 2014 and issued as U.S. Pat. No. 9,532,783 on Jan. 3, 2017.

BACKGROUND

In some settings, a surgeon may want to position a surgical instrument through an orifice of the patient and use the instrument to adjust, position, attach, and/or otherwise interact with tissue within the patient. For instance, in some surgical procedures, portions of the gastrointestinal tract may be cut and removed to eliminate undesirable tissue or for other reasons. Once the desired tissue is removed, the remaining portions may need to be recoupled together. One such tool for accomplishing these anastomotic procedures is a circular stapler that is inserted through a patient's orifice.

Examples of circular surgical staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996. The disclosure of each of the above-cited U.S. Patents is incorporated by reference herein. Some such staplers are operable to clamp down on layers of tissue, cut through the clamped layers of tissue, and drive staples through the layers of tissue to substantially seal the severed layers of tissue together near the severed ends of the tissue layers, thereby joining two severed ends of an anatomical lumen.

Merely additional other exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; and U.S. Pat. No. 7,721,930, entitled "Disposable Cartridge with Adhesive for Use with a Stapling Device," issued May 25, 2010. The disclosure of each of the above-cited U.S. Patents is incorporated by reference herein. While the surgical staplers referred to above are described as being used in endoscopic procedures, it should be understood that such surgical staplers may also be used in open procedures and/or other non-endoscopic procedures.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 2C depicts an enlarged longitudinal cross-sectional view of the stapling head assembly of FIG. 2A showing an exemplary staple driver and blade in a fired position;

FIG. 3 depicts an enlarged partial cross-sectional view of an exemplary staple formed against the anvil;

FIG. 9 depicts a cross sectional view of the handle assembly of the instrument of FIG. 7;

FIG. 10 depicts an enlarged, partial cross sectional view of the motor and battery assemblies of FIG. 7;

Figure 6:
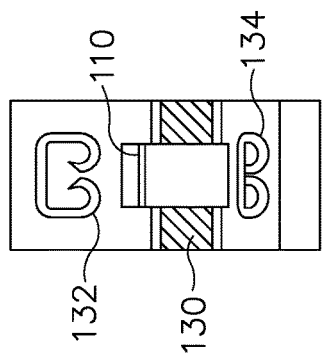
FIG. 6 depicts an diagrammatic view of the indicator window of FIG. 5 showing an exemplary indicator bar and exemplary corresponding staple representations.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Circular Stapling Surgical Instrument

FIGS. 1-6 depict an exemplary circular surgical stapling instrument (10) having a stapling head assembly (20), a shaft assembly (60), and an actuator handle assembly (70), each of which will be described in more detail below. Shaft assembly (60) extends distally from actuator handle assembly (70) and stapling head assembly (20) is coupled to a distal end of shaft assembly (60). In brief, actuator handle assembly (70) is operable to actuate a staple driver (24) of stapling head assembly (20) to drive a plurality of staples (66) out of stapling head assembly (20). Staples (66) are bent to form completed staples by an anvil (40) that is attached at the distal end of instrument (10). Accordingly, tissue (2), shown in FIGS. 2A-2C, may be stapled utilizing instrument (10).

In the present example, instrument (10) comprises a closure system and a firing system. The closure system comprises a trocar (38), a trocar actuator (39), and a rotating knob (98). An anvil (40) may be coupled to a distal end of trocar (38). Rotating knob (98) is operable to longitudinally translate trocar (38) relative to stapling head assembly (20), thereby translating anvil (40) when anvil (40) is coupled to trocar (38), to clamp tissue between anvil (40) and stapling head assembly (20). The firing system comprises a trigger (74), a trigger actuation assembly (84), a driver actuator (64), and a staple driver (24). Staple driver (24) includes a knife (36) configured to sever tissue when staple driver (24) is actuated longitudinally. In addition, staples (66) are positioned distal to a plurality of staple driving members (30) of staple driver (24) such that staple driver (24) also drives staples (66) distally when staple driver (24) is actuated longitudinally. Thus, when trigger (74) is actuated and trigger actuation assembly (84) actuates staple driver (24) via driver actuator (64), knife (36) and members (30) substantially simultaneously sever tissue (2) and drive staples (66) distally relative to stapling head assembly (20) into tissue. The components and functionalities of the closure system and firing system will now be described in greater detail.

A. Exemplary Anvil

Figure 1:
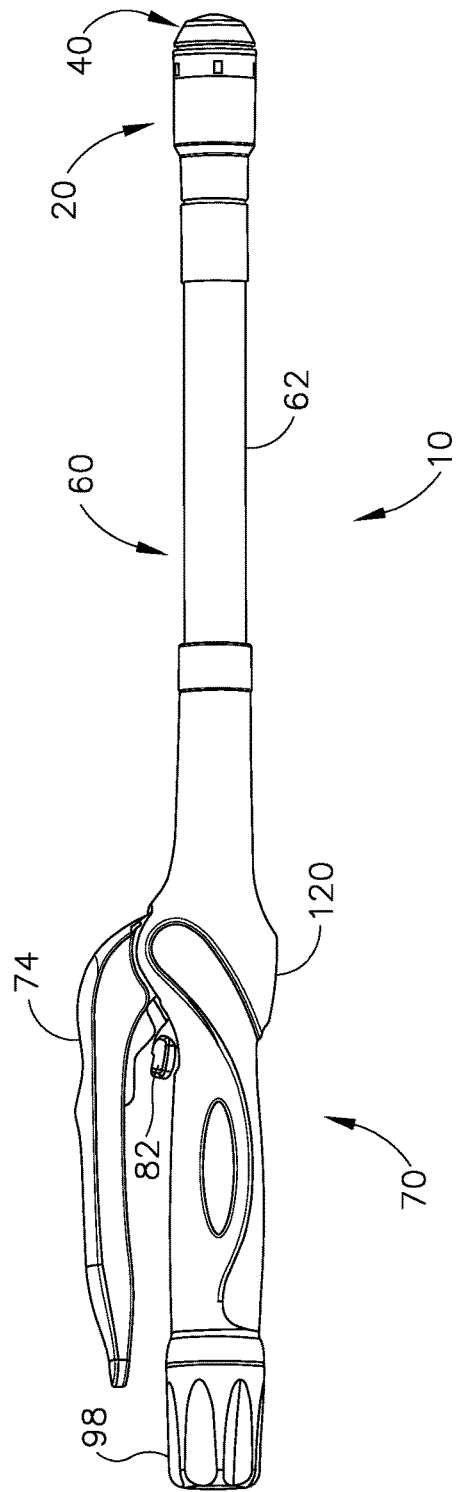
FIG. 1 depicts a side elevation view of an exemplary circular stapling surgical instrument.
Figure 2A:
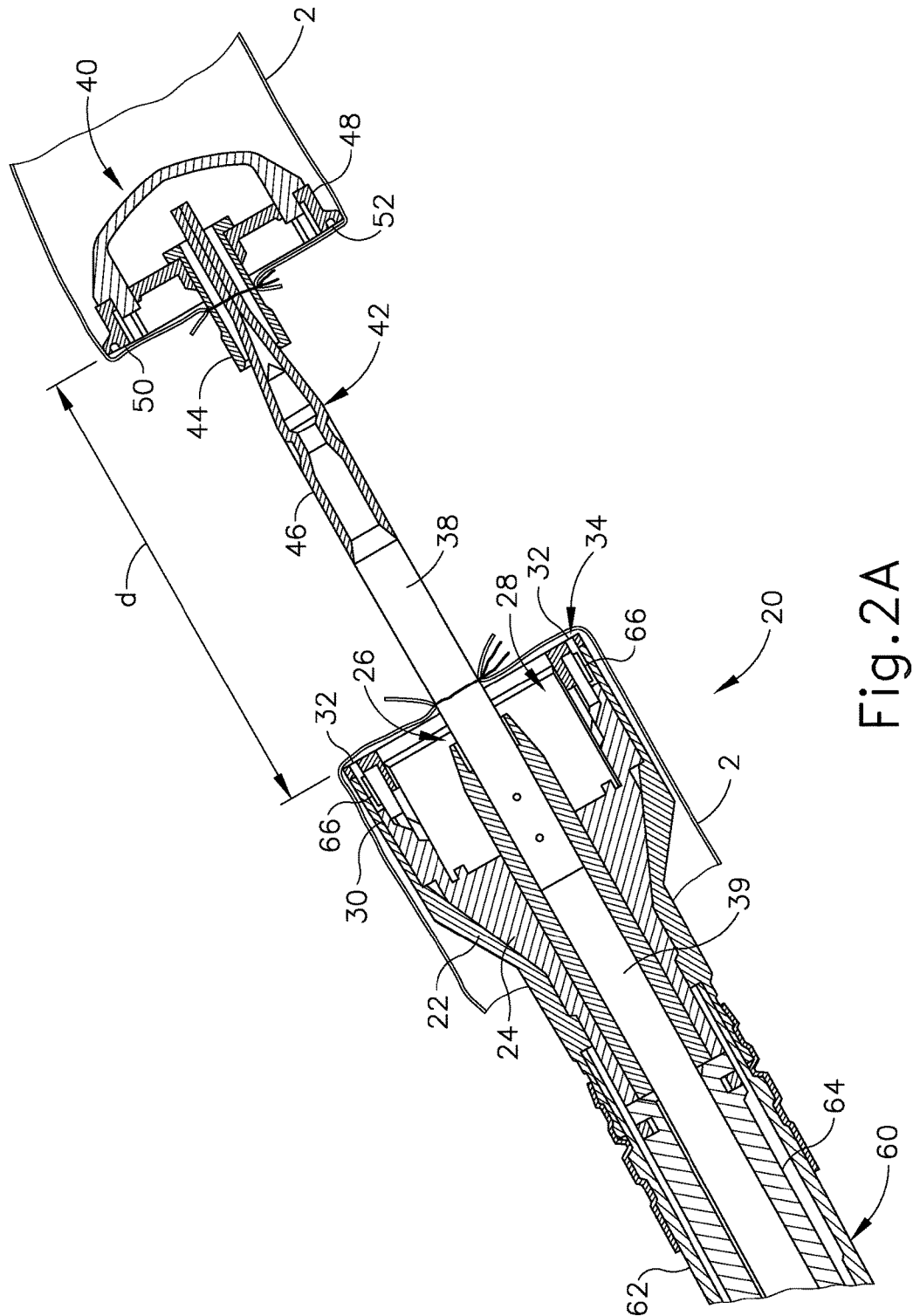
FIG. 2A depicts an enlarged longitudinal cross-section view of an exemplary stapling head assembly of the instrument of FIG. 1 showing an exemplary anvil in an open position.
Figure 2B:
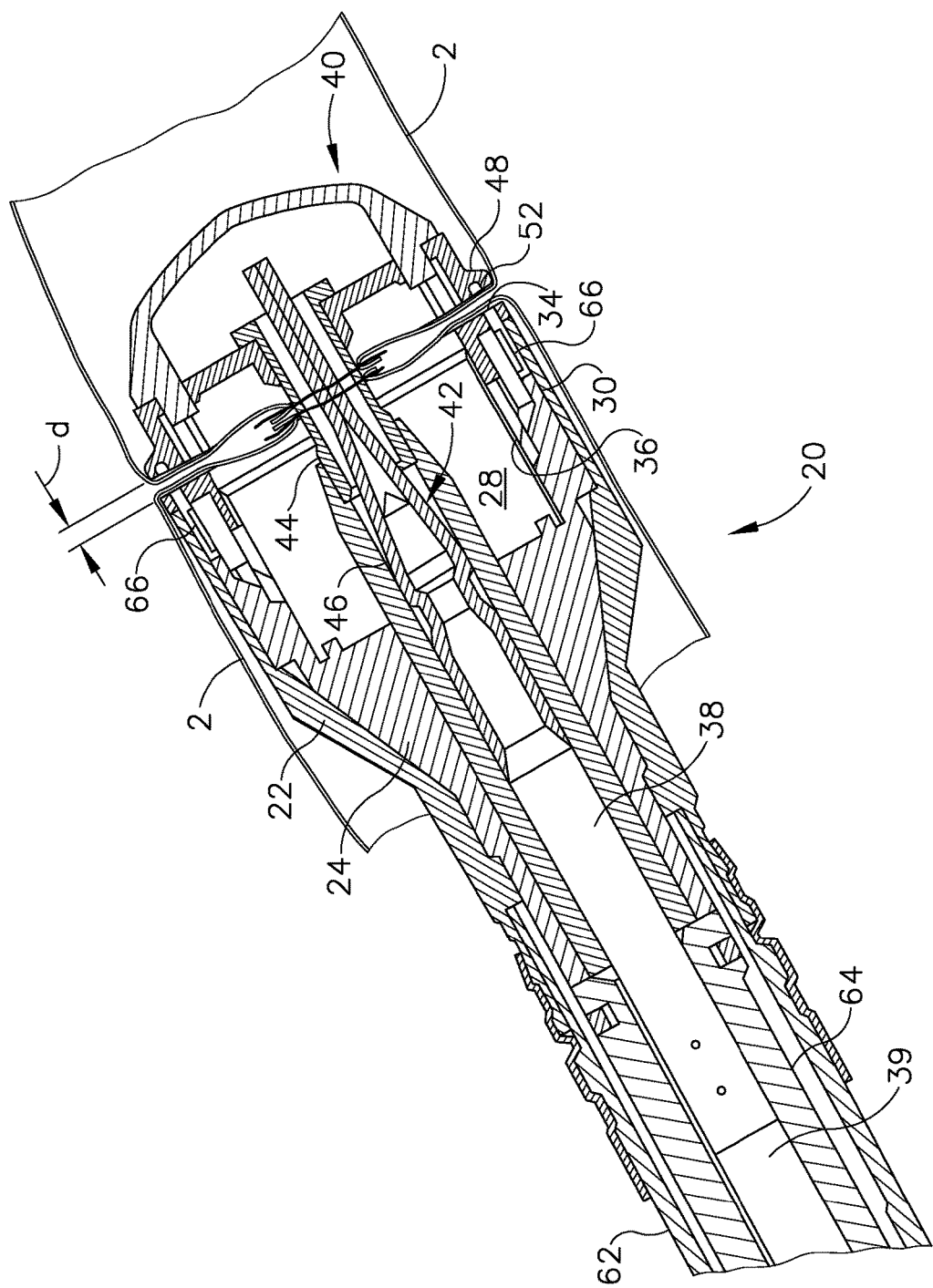
FIG. 2B depicts an enlarged longitudinal cross-sectional view of the stapling head assembly of FIG. 2A showing the anvil in a closed position.

As shown in FIGS. 1-2C, anvil (40) is selectively coupleable to instrument (10) to provide a surface against which staples (66) may be bent to staple material contained between stapling head assembly (20) and anvil (40). Anvil (40) of the present example is selectively coupleable to a trocar or pointed rod (38) that extends distally relative to stapling head assembly (20). Referring to FIGS. 2A-2C, anvil (40) is selectively coupleable via the coupling of a proximal shaft (42) of anvil (40) to a distal tip of trocar (38). Anvil (40) comprises a generally circular anvil head (48) and a proximal shaft (42) extending proximally from anvil head (48). In the example shown, proximal shaft (42) comprises a tubular member (44) having resiliently biased retaining clips (46) to selectively couple anvil (40) to trocar (38), though this is merely optional, and it should be understood that other retention features for coupling anvil (40) to trocar (38) may be used as well. For example, C-clips, clamps, threading, pins, adhesives, etc. may be employed to couple anvil (40) to trocar (38). In addition, while anvil (40) is described as selectively coupleable to trocar (38), in some versions proximal shaft (42) may include a one-way coupling feature such that anvil (40) cannot be removed from trocar (38) once anvil (40) is attached. Merely exemplary one-way features include barbs, one way snaps, collets, collars, tabs, bands, etc. Of course still other configurations for coupling anvil (40) to trocar (38) will be apparent to one of ordinary skill in the art in view of the teachings herein. For instance, trocar (38) may instead be a hollow shaft and proximal shaft (42) may comprise a sharpened rod that is insertable into the hollow shaft.

Anvil head (48) of the present example comprises a plurality of staple forming pockets (52) formed in a proximal face (50) of anvil head (48). Accordingly, when anvil (40) is in the closed position and staples (66) are driven out of stapling head assembly (20) into staple forming pockets (52), as shown in FIG. 2C, legs (68) of staples (66) are bent to form completed staples.

With anvil (40) as a separate component, it should be understood that anvil (40) may be inserted and secured to a portion of tissue (2) prior to being coupled to stapling head assembly (20). By way of example only, anvil (40) may be inserted into and secured to a first tubular portion of tissue (2) while instrument (10) is inserted into and secured to a second tubular portion of tissue (2). For instance, the first tubular portion of tissue (2) may be sutured to or about a portion of anvil (40), and the second tubular portion of tissue (2) may be sutured to or about trocar (38).

As shown in FIG. 2A, anvil (40) is then coupled to trocar (38). Trocar (38) of the present example is shown in a distal most actuated position. Such an extended position for trocar (38) may provide a larger area to which tissue (2) may be coupled prior to attachment of anvil (40). In addition, the extended position of trocar (38) may also provide for easier attachment of anvil (40) to trocar (38). Trocar (38) further includes a tapered distal tip. Such a tip may be capable of piercing through tissue and/or aiding the insertion of anvil (40) on to trocar (38), though the tapered distal tip is merely optional. For instance, in other versions trocar (38) may have a blunt tip. In addition, or in the alternative, trocar (38) may include a magnetic portion (not shown) which may attract anvil (40) towards trocar (38). Of course still further configurations and arrangements for anvil (40) and trocar (38) will be apparent to one of ordinary skill in the art in view of the teachings herein.

When anvil (40) is coupled to trocar (38), the distance between a proximal face of the anvil (40) and a distal face of stapling head assembly (20) defines a gap distance d. Trocar (38) of the present example is translatable longitudinally relative to stapling head assembly (20) via an adjusting knob (98) located at a proximal end of actuator handle assembly (70), as will be described in greater detail below. Accordingly, when anvil (40) is coupled to trocar (38), rotation of adjusting knob (98) enlarges or reduces gap distance d by actuating anvil (40) relative to stapling head assembly (20). For instance, as shown sequentially in FIGS. 2A-2B, anvil (40) is shown actuating proximally relative to actuator handle assembly (70) from an initial, open position to a closed position, thereby reducing the gap distance d and the distance between the two portions of tissue (2) to be joined. Once the gap distance d is brought within a predetermined range, stapling head assembly (20) may be fired, as shown in FIG. 2C, to staple and sever tissue (2) between anvil (40) and stapling head assembly (20). Stapling head assembly (20) is operable to staple and sever tissue (2) by a user pivoting a trigger (74) of actuator handle assembly (70), as will be described in greater detail below.

Figure 5:
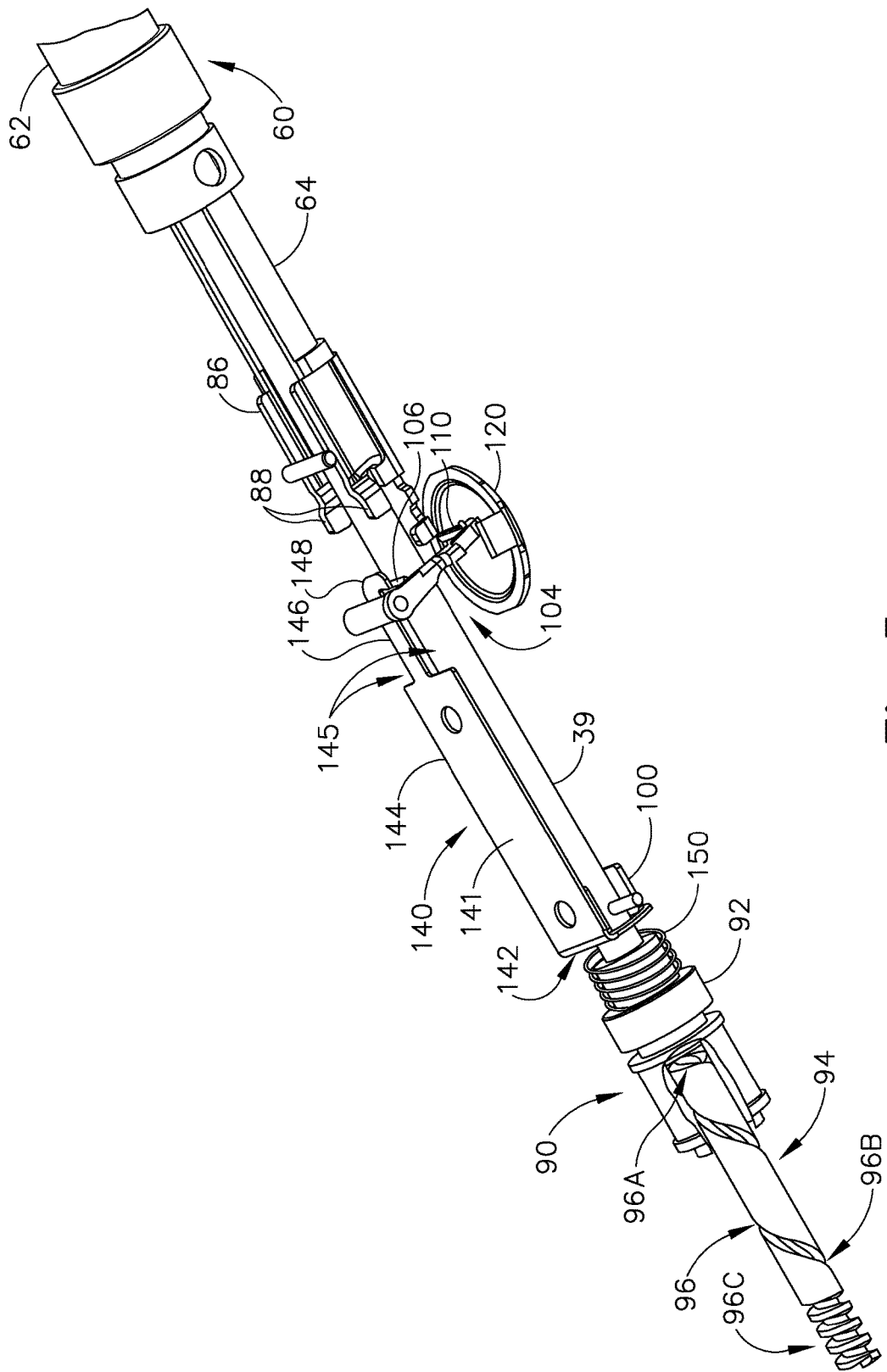
FIG. 5 depicts an enlarged partial perspective view of an exemplary indicator assembly of the surgical instrument of FIG. 1 showing an indicator window and indicator lever.

As noted above, gap distance d corresponds to the distance between anvil (40) and stapling head assembly (20). When instrument (10) is inserted into a patient, this gap distance d may not be easily viewable. Accordingly, a moveable indicator bar (110), shown in FIGS. 5-6, is provided to be visible through an indicator window (120) positioned opposite to trigger (74). Indicator bar (110) is operable to move in response to rotation of adjusting knob (98) such that the position of indicator bar (110) is representative of the gap distance d. As shown in FIG. 6, indicator window (120) further comprises a scale (130) which indicates that the anvil gap is within a desired operating range (e.g., a green colored region or "green zone") and a corresponding staple compression representation at each end of scale (130). By way of example only, as shown in FIG. 6, a first staple image (132) depicts a large staple height while a second staple image (134) depicts a small staple height. Accordingly, a user can view the position of the coupled anvil (40) relative to the stapling head assembly (20) via indicator bar (110) and scale (130). The user may then adjust the positioning of anvil (40) via adjusting knob (98) accordingly.

Referring back to FIGS. 2A-2C, a user sutures a portion of tissue (2) about tubular member (44) such that anvil head (48) is located within a portion of the tissue (2) to be stapled. When tissue (2) is attached to anvil (40), retaining clips (46) and a portion of tubular member (44) protrude out from tissue (2) such that the user may couple anvil (40) to trocar (38). With tissue (2) coupled to trocar (38) and/or another portion of stapling head assembly (20), the user attaches anvil (40) to trocar (38) and actuates anvil (40) proximally towards stapling head assembly (20) to reduce the gap distance d. Once instrument (10) is within the operating range, the user then staples together the ends of tissue (2), thereby forming a substantially contiguous tubular portion of tissue (2).

Anvil (40) may be further constructed in accordance with at least some of the teachings of U.S. Pat. Nos. 5,205,459; 5,271,544; 5,275,322; 5,285,945; 5,292,053; 5,333,773; 5,350,104; 5,533,661, the disclosures of which are incorporated by reference herein; and/or in accordance with other configurations as will be apparent to one of ordinary skill in the art in view of the teachings herein.

B. Exemplary Stapling Head Assembly

Stapling head assembly (20) of the present example is coupled to a distal end of shaft assembly (60) and comprises a tubular casing (22) housing a slidable staple driver (24) and a plurality of staples (66) contained within staple pockets (32). Staples (66) and staple pockets (32) are disposed in a circular array about tubular casing (22). In the present example, staples (66) and staple pockets (32) are disposed in a pair of concentric annular rows of staples (66) and staple pockets (32). Staple driver (24) is operable to actuate longitudinally within tubular casing (22) in response to rotation of trigger (74) of actuator handle assembly (70). As shown in FIGS. 2A-2C, staple driver (24) comprises a flared cylindrical member having a trocar opening (26), a central recess (28), and a plurality of members (30) disposed circumferentially about central recess (28) and extending distally relative to shaft assembly (60). Each member (30) is configured to contact and engage a corresponding staple (66) of the plurality of staples (66) within staple pockets (32). Accordingly, when staple driver (24) is actuated distally relative to actuator handle assembly (70), each member (30) drives a corresponding staple (66) out of its staple pocket (32) through a staple aperture (34) formed in a distal end of tubular casing (22). Because each member (30) extends from staple driver (24), the plurality of staples (66) are driven out of stapling head assembly (20) at substantially the same time. When anvil (40) is in the closed position, staples (66) are driven into staple forming pockets (52) to bend legs (68) of the staples (66), thereby stapling the material located between anvil (40) and stapling head assembly (20). FIG. 3 depicts one merely exemplary staple (66) driven by a member (30) into a staple forming pocket (32) of anvil (40) to bend legs (68).

Staple driver (24) further includes a cylindrical knife (36) that is coaxial to trocar opening (26) and inset from staple pockets (32). In the present example, cylindrical knife (36) is disposed within central recess (28) to translate distally with staple driver (24). When anvil (40) is secured to trocar (38), as described above, anvil head (48) provides a surface against which cylindrical knife (36) cuts the material contained between anvil (40) and stapling head assembly (20). In some versions, anvil head (48) may include a recess (not shown) for cylindrical knife (36) to aid in cutting the material (e.g., by providing a cooperative shearing edge). In addition, or in the alternative, anvil head (48) may include one or more opposing cylindrical knives (not shown) offset from cylindrical knife (36) such that a scissor-type cutting action may be provided. Still other configurations will be apparent to one of ordinary skill in the art in view of the teachings herein. Stapling head assembly (20) is thus operable to both staple and cut tissue (2) substantially simultaneously in response to actuation by actuator handle assembly (70).

Of course stapling head assembly (20) may be further constructed in accordance with at least some of the teachings of U.S. Pat. Nos. 5,205,459; 5,271,544; 5,275,322; 5,285,945, 5,292,053; 5,333,773; 5,350,104; 5,533,661, the disclosures of which are incorporated by reference herein; and/or in accordance with other configurations as will be apparent to one of ordinary skill in the art in view of the teachings herein.

As noted previously, staple driver (24) includes a trocar opening (26). Trocar opening (26) is configured to permit trocar (38) to longitudinally slide relative to stapling head assembly (20) and/or shaft assembly (60). As shown in FIGS. 2A-2C, trocar (38) is coupled to a trocar actuator (39) such that trocar (38) can be actuated longitudinally via rotation of rotating knob (98), as will be described in greater detail below in reference to actuator handle assembly (70). In the present example, trocar actuator (39) comprises an elongated, relatively stiff shaft coupled to trocar (38), though this is merely optional. In some versions, actuator (39) may comprise a longitudinally stiff material while permitting lateral bending such that portions of instrument (10) may be selectively bent or curved during use; or instrument (10) may include a preset bent shaft assembly (60). One merely exemplary material is nitinol. When anvil (40) is coupled to trocar (38), trocar (38) and anvil (40) are translatable via actuator (39) to adjust the gap distance d between anvil (40) and stapling head assembly (20). Still further configurations for actuator (39) to longitudinally actuate trocar (38) will be apparent to one of ordinary skill in the art in view of the teachings herein.

C. Exemplary Shaft Assembly

Stapling head assembly (20) and trocar (38) are positioned at a distal end of shaft assembly (60), as shown in FIGS. 2A-2C. Shaft assembly (60) of the present example comprises an outer tubular member (62) and a driver actuator (64). Outer tubular member (62) is coupled to tubular casing (22) of stapling head assembly (20) and to a body (72) of actuator handle assembly (70), thereby providing a mechanical ground for the actuating components therein. The proximal end of driver actuator (64) is coupled to a trigger actuation assembly (84) of actuator handle assembly (70), described below. The distal end of driver actuator (64) is coupled to staple driver (24) such that the rotation of trigger (74) longitudinally actuates staple driver (24). As shown in FIGS. 2A-2C, driver actuator (64) comprises a tubular member having an open longitudinal axis such that actuator (39) coupled to trocar (38) may actuate longitudinally within and relative to driver actuator (64). Of course it should be understood that other components may be disposed within driver actuator (64) as will be apparent to one of ordinary skill in the art in view of the teachings herein.

Shaft assembly (60) may be further constructed in accordance with at least some of the teachings of U.S. Pat. Nos. 5,205,459; 5,271,544; 5,275,322; 5,285,945; 5,292,053; 5,333,773; 5,350,104; 5,533,661, the disclosures of which are incorporated by reference herein; and/or in accordance with other configurations as will be apparent to one of ordinary skill in the art in view of the teachings herein.

D. Exemplary Actuator Handle Assembly

Figure 4A:
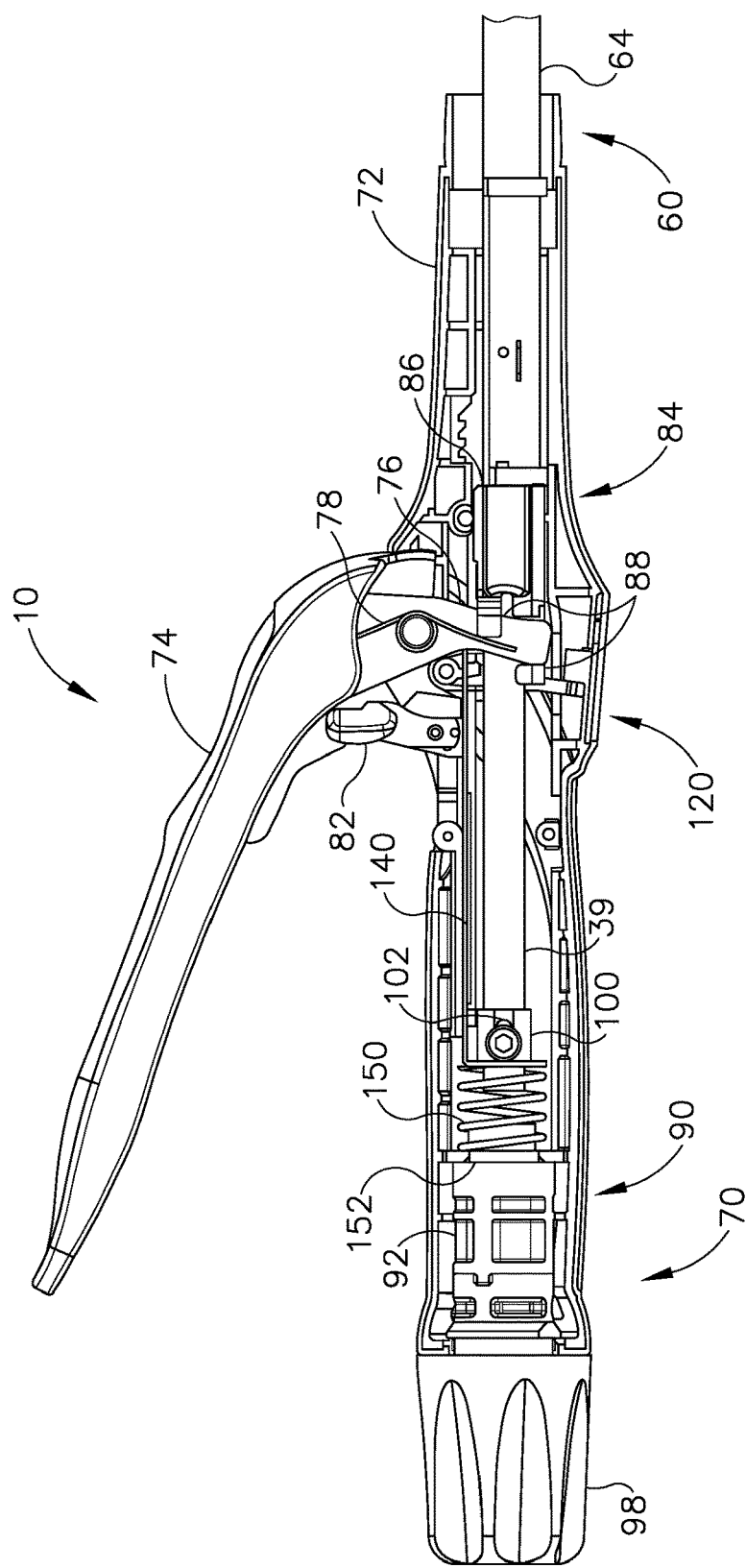
FIG. 4A depicts an enlarged side elevation view of an exemplary actuator handle assembly of the surgical instrument of FIG. 1 with a portion of the body removed, showing a trigger in an unfired position and a lockout feature in a locked position.
Figure 4B:
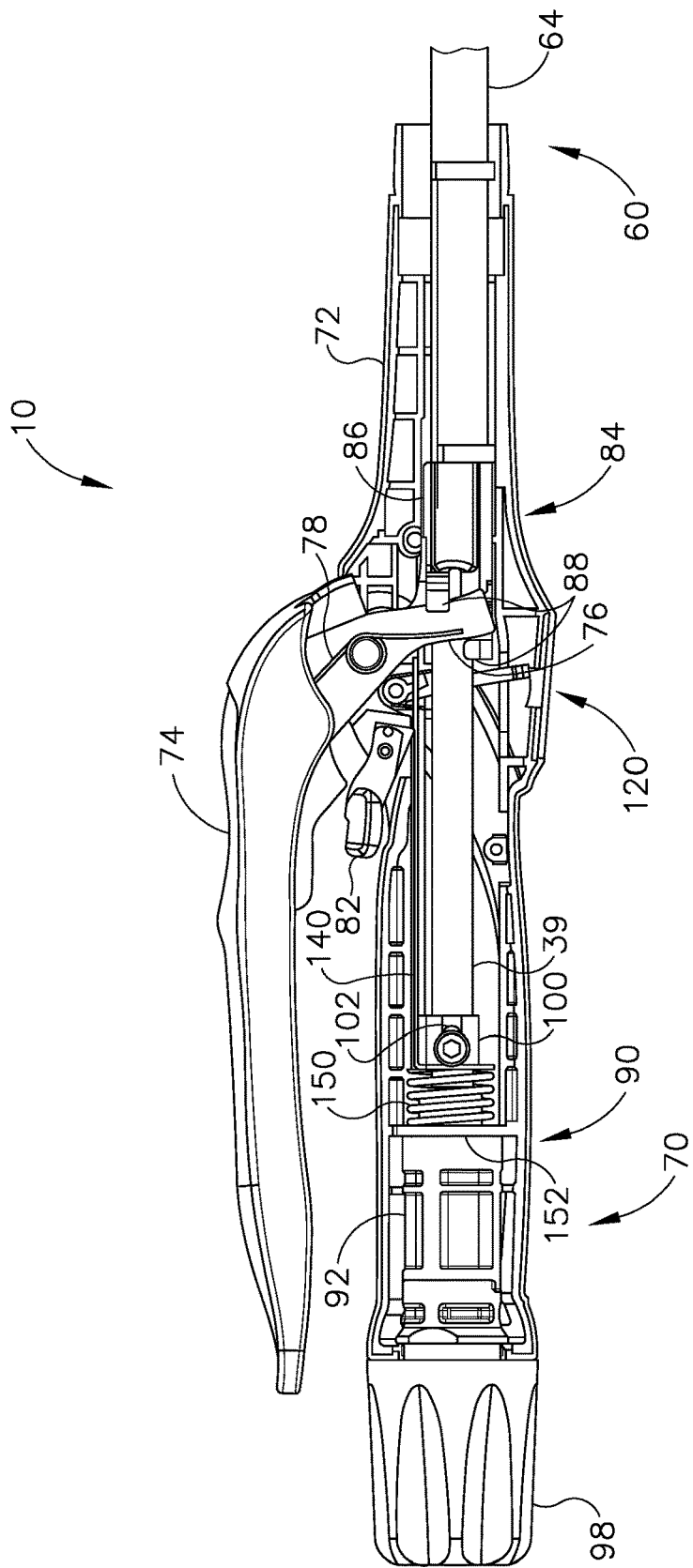
FIG. 4B depicts an enlarged side elevation view of the actuator handle assembly of FIG. 4A, showing the trigger in a fired position and the lockout feature in an unlocked position.

Referring now to FIGS. 4A-5, actuator handle assembly (70) comprises a body (72), a trigger (74), a lockout feature (82), a trigger actuation assembly (84), and a trocar actuation assembly (90). Trigger (74) of the present example is pivotably mounted to body (72) and is coupled to trigger actuation assembly (84) such that rotation of trigger (74) from an unfired position (shown in FIG. 4A) to a fired position (shown in FIG. 4B) actuates driver actuator (64) described above. A spring (78) is coupled to body (72) and trigger (74) to bias trigger (74) towards the unfired position.

Lockout feature (82) is a pivotable member that is coupled to body (72). In a first, locked position, lockout feature (82) is pivoted upwards and away from body (72) such that lockout feature (82) engages trigger (74) and mechanically resists actuation of trigger (74) by a user. In a second, unlocked position, such as that shown in FIGS. 1 and 4B, lockout feature (82) is pivoted downward such that trigger (74) may be actuated by the user. Accordingly, with lockout feature (82) in the second position, trigger (74) can engage a trigger actuation assembly (84) to fire instrument (10).

As shown in FIGS. 4A-4B, trigger actuation assembly (84) of the present example comprises a slidable trigger carriage (86) engaged with a proximal end of driver actuator (64). Carriage (86) includes a set of tabs (88) on a proximal end of carriage (86) to retain and engage a pair of trigger arms (76) extending from trigger (74). Accordingly, when trigger (74) is pivoted, carriage (86) is actuated longitudinally and transfers the longitudinal motion to driver actuator (64). In the example shown, carriage (86) is fixedly coupled to the proximal end of driver actuator (64), though this is merely optional. Indeed, in one merely exemplary alternative, carriage (86) may simply abut driver actuator (64) while a distal spring (not shown) biases driver actuator (64) proximally relative to actuator handle assembly (70).

Trigger actuation assembly (84) may be further constructed in accordance with at least some of the teachings of U.S. Pat. Nos. 5,205,459; 5,271,544; 5,275,322; 5,285,945; 5,292,053; 5,333,773; 5,350,104; 5,533,661, the disclosures of which are incorporated by reference herein; and/or in accordance with other configurations as will be apparent to one of ordinary skill in the art in view of the teachings herein.

Body (72) also houses a trocar actuation assembly (90) configured to actuate trocar (38) longitudinally in response to rotation of adjusting knob (98). As best shown in FIGS. 4A-5, trocar actuation assembly (90) of the present example comprises adjusting knob (98), a grooved shank (94), and a sleeve (92). Grooved shank (94) of the present example is located at a distal end of trocar actuator (39), though it should be understood that grooved shank (94) and trocar actuator (39) may alternatively be separate components that engage to transmit longitudinal movement. Adjusting knob (98) is rotatably supported by the proximal end of body (72) and is operable to rotate sleeve (92) that is engaged with grooved shank (94) via an internal tab (not shown). Grooved shank (94) of the present example comprises a continuous groove (96) formed in the outer surface of grooved shank (94). Accordingly, when adjusting knob (98) is rotated, the internal tab rides within groove (96) and grooved shank (94) is longitudinally actuated relative to sleeve (92). Since grooved shank (94) is located at the distal end of trocar actuator (39), rotating adjusting knob (98) in a first direction advances trocar actuator (39) distally relative to actuator handle assembly (70). Accordingly, the gap distance d between anvil (40) and stapling head assembly (20) is increased. By rotating adjusting knob (98) in the opposite direction, trocar actuator (39) is actuated proximally relative to actuator handle assembly (70) to reduce the gap distance d between anvil (40) and stapling head assembly (20). Thus, trocar actuation assembly (90) is operable to actuate trocar (38) in response to rotating adjustment knob (98). Of course other configurations for trocar actuation assembly (90) will be apparent to one of ordinary skill in the art in view of the teachings herein.

Groove (96) of the present example comprises a plurality of different portions (96A, 96B, 96C) that have a varying pitch or number of grooves per axial distance. The present groove (96) is divided into a distal portion (96A), a middle portion (96B) and a proximal portion (96C). As shown in FIG. 5, distal portion (96A) comprises a fine pitch or a high number of grooves over a short axial distance of grooved shank (94) such that a large number of rotations of adjusting knob (98) are required to traverse the short axial distance. Middle portion (96B) comprises a section with comparably coarser pitch or fewer grooves per axial distance such that relatively few rotations are required to traverse a long axial distance. Accordingly, the gap distance d may be quickly reduced through relatively few rotations of adjusting knob (98). Proximal portion (96C) of the present example is substantially similar to distal portion (96A) and comprises a fine pitch or a high number of grooves over a short axial distance of grooved shank (94) such that a large number of rotations are required to traverse the short axial distance. Proximal portion (96C) of the present example is positioned within sleeve (92) when anvil (40) is substantially near to stapling head assembly (20) such that indicator bar (110) moves within indicator window (120) along scale (130) to indicate that the anvil gap is within a desired operating range, as will be described in more detail below. Accordingly, when the tab is within proximal portion (96C) of groove (96), each rotation of adjusting knob (98) may reduce the gap distance d by a small amount to provide for fine tuning.

Trocar actuation assembly (90) may be further constructed in accordance with at least some of the teachings of U.S. Pat. Nos. 5,205,459; 5,271,544; 5,275,322; 5,285,945; 5,292,053; 5,333,773; 5,350,104; 5,533,661, the disclosures of which are incorporated by reference herein; and/or in accordance with other configurations as will be apparent to one of ordinary skill in the art in view of the teachings herein.

In the example shown in FIGS. 4A-4B, a U-shaped clip (100) is attached to an intermediate portion of trocar actuator (39) located distally of grooved shank (94). In the present example, an extension of trocar actuator (39) engages a slot in the housing of handle assembly (70) to prevent trocar actuator (39) from rotating about its axis when adjusting knob (98) is rotated. In some other versions, U-shaped clip (100) engages with a portion of body (72) to substantially prevent trocar actuator (39) from rotating about its axis when adjusting knob (98) is rotated. U-shaped clip (100) of the present example further includes an elongated slot (102) on each of its opposite sides for receiving an attachment member, such as a screw, bolt, pin, clip, etc., to selectively adjust the longitudinal position of elongated slot (102) of U-shaped clip (100) relative to trocar actuator (39) for purposes of calibrating indicator bar (110) relative to scale (130).

As shown in FIG. 5, actuator handle assembly (70) further includes an indicator bracket (140) configured to engage and pivot an indicator (104). Indicator bracket (140) of the present example is slidable relative to body (72) along a pair of slots formed on body (72). Indicator bracket (140) comprises a rectangular plate (144), an indicator arm (146), and an angled flange (142). Angled flange (142) is formed at the proximal end of rectangular plate (144) and includes an aperture (not shown) to slidable mount onto trocar actuator (39) and/or grooved shank (94). A coil spring (150) is interposed between flange (142) and a boss (152) to bias flange (142) against U-shaped clip (100). Accordingly, when U-shaped clip (100) actuates distally with trocar actuator (39) and/or grooved shank (94), coil spring (150) urges indicator bracket (140) to travel distally with U-shaped clip (100). In addition, U-shaped clip (100) urges indicator bracket (140) proximally relative to boss (152) when trocar actuator (39) and/or grooved shank (94) translate proximally, thereby compressing coil spring (150). Of course, it should be understood that in some versions indicator bracket (140) may be fixedly attached to trocar actuator (39) and/or grooved shank (94).

In the present example, a portion of lockout feature (82) abuts a surface (141) of indicator bracket (140) when indicator bracket (140) is in a longitudinal position that does not correspond to when the anvil gap is within a desired operating range (e.g., a green colored region or "green zone"). When the anvil gap is within a desired operating range (e.g., a green colored region or "green zone"), indicator bracket (140) narrows to provide a pair of gaps (145) on either side of an indicator arm (146) that permits lockout feature (82) to pivot, thereby releasing trigger (74). Accordingly, lockout feature (82) and indicator bracket (140) can substantially prevent a user from releasing and operating trigger (74) until anvil (40) is in a predetermined operating range. Of course it should be understood that lockout feature (82) may be omitted entirely in some versions.

This operating range may be visually communicated to the user via an indicator bar (110) of an indicator (104) shown against a scale (130), described briefly above. At the distal end of indicator bracket (140) is a distally projecting indicator arm (146) which terminates at a laterally projecting finger (148) for controlling the movement of indicator (104). Indicator arm (146) and finger (148), best shown in FIG. 5, are configured to engage a tab (106) of indicator (104) such that indicator (104) is pivoted when indicator bracket (140) is actuated longitudinally. In the present example, indicator (104) is pivotably coupled to body (72) at a first end of indicator (104), though this is merely optional and other pivot points for indicator (104) will be apparent to one of ordinary skill in the art in view of the teachings herein. An indicator bar (110) is positioned on the second end of indicator (104) such that indicator bar (110) moves in response to the actuation of indicator bracket (140). Accordingly, as discussed above, indicator bar (110) is displayed through an indicator window (120) against a scale (130) (shown in FIG. 6) to show the relative gap distance d between anvil (40) and stapling head assembly (20).

Of course indicator bracket (140), indicator (104), and/or actuator handle assembly (70) may be further constructed in accordance with at least some of the teachings of U.S. Pat. Nos. 5,205,459; 5,271,544; 5,275,322; 5,285,945; 5,292,053; 5,333,773; 5,350,104; 5,533,661, the disclosures of which are incorporated by reference herein; and/or in accordance with other configurations as will be apparent to one of ordinary skill in the art in view of the teachings herein.

II. Exemplary Motorized Circular Stapling Surgical Instrument with Selectable Control In some instances, it may be desirable to provide motorized control of instrument (10). It may further be desirable to enable a user to select between either motorized control or manual control of a motorized version of circular surgical stapling instrument (10). For example, instrument (10) may include an operational mode selection assembly that allows the user to disengage an automated, motorized rotary actuation system and provide manual actuation of that system. It may also be desirable to provide a switch assembly for changing the mode of a single rotary drive between a tissue clamping mode and a tissue cutting/stapling mode. In other words, such a switch assembly may enable a single rotary drive to either actuate anvil (40) clamping features or actuate knife (36) and staple driving features of instrument (10). The examples below include merely illustrative versions of instrument (10) where a single motor can be used to control both clamping and cutting/stapling of tissue via a single rotary drive; where the operator can select between motorized operation and manual operation; and a stapling head cartridge assembly that is responsive to the single rotary drive in motorized and manual operation.

A. Exemplary Operational Mode Selection Assembly

Figure 7:
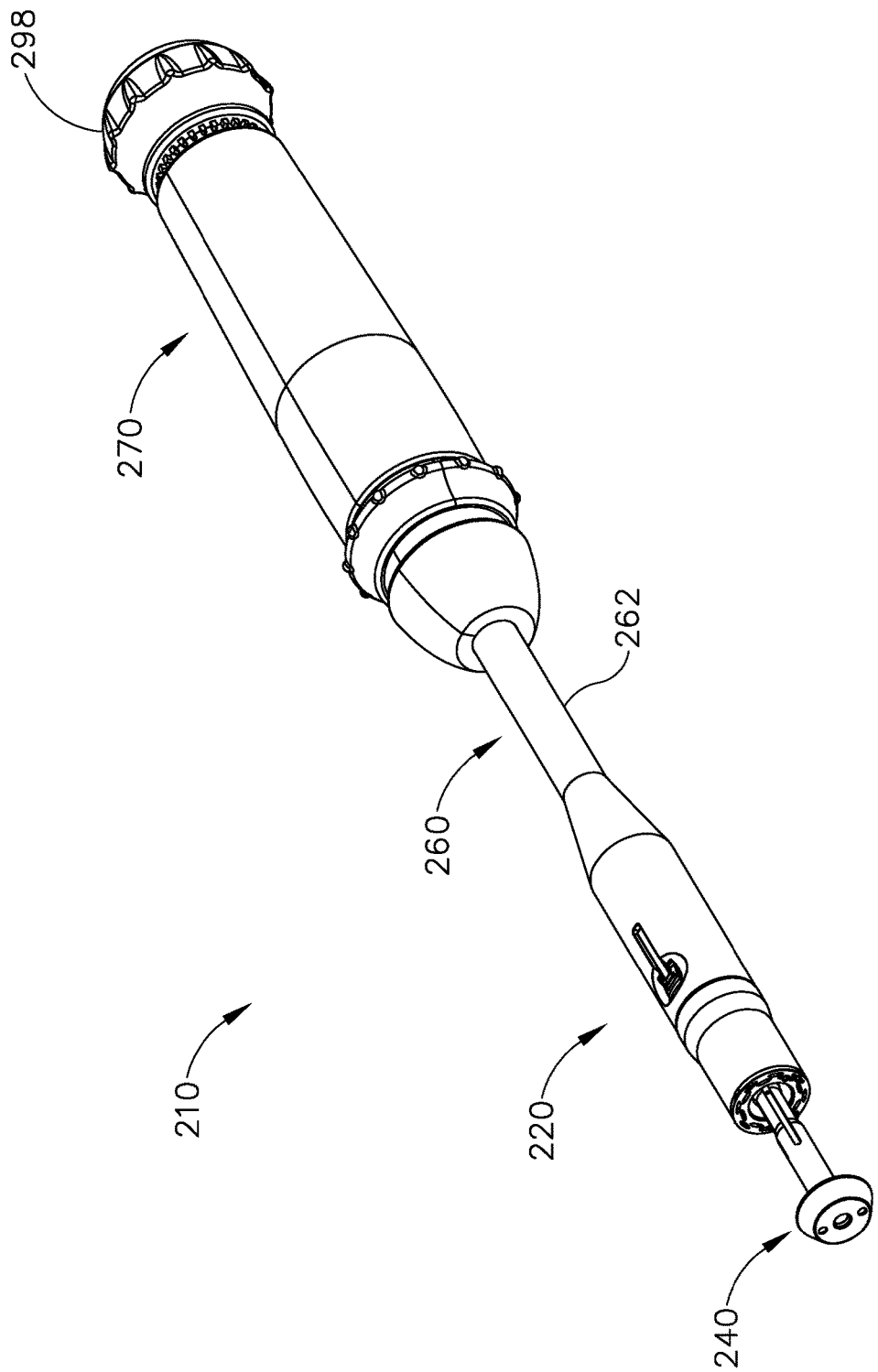
FIG. 7 depicts a perspective view of another exemplary circular stapling surgical instrument.

FIG. 7 shows another exemplary circular stapling instrument (210), which is a selectively motorized variation of instrument (10). Instrument (210) of this example comprises a stapling head assembly (220), an anvil (240), a shaft assembly (260), and a handle assembly (270). Stapling head assembly (220) is similar to stapling head assembly (20) in that stapling head assembly (220) selectively couples with anvil (240). Stapling head assembly (220) is operable to clamp tissue between staple pockets (32) and staple forming pockets (52) of anvil (240). Stapling head assembly (220) comprises a cylindrical knife (36) that is operable to sever tissue captured between stapling head assembly (220) and anvil (240). Stapling head assembly (220) drives staples (66) through the tissue captured between stapling head assembly (220) and anvil (240). Stapling instrument (210) may be used to create a secure anastomosis (e.g., an end-to-end anastomosis) within a gastro-intestinal tract of a patient or elsewhere.

Stapling head assembly (220) differs from stapling head assembly (20) in that stapling head assembly (220) is operable to clamp tissue, sever tissue, and staple tissue all in response to a single rotary input communicated via shaft assembly (260). Accordingly, actuation inputs translated linearly through shaft assembly (260) are not required for stapling head assembly (220), though stapling head assembly (220) may comprise a translating clutch feature. By way of example only, at least part of stapling head assembly (220) may be configured in accordance with at least some of the teachings of U.S. patent application Ser. No. 13/716,318, entitled "Motor Driven Rotary Input Circular Stapler with Modular End Effector," filed on Dec. 17, 2012 (published as U.S. Pub. No. 2014/0166728 on Jun. 19, 2014), issued as U.S. Pat. No. 9,597,081 on Mar. 21, 2017, the disclosure of which is incorporated by reference herein. Other suitable configurations for stapling head assembly (220) will be apparent to those of ordinary skill in the art in view of the teachings herein.

Shaft assembly (260) is similar to shaft assembly (60) in that shaft assembly (260) couples handle assembly (270) with stapling head assembly (220). Shaft assembly (260) differs from shaft assembly (60) in that shaft assembly (260) comprises a single actuation feature, rotary driver actuator (264) shown in FIG. 8. Driver actuator (264) is operable to drive stapling head assembly (220) to clamp tissue, sever tissue, and staple tissue. Accordingly, linear actuation through shaft assembly (260) is not required, though rotary driver actuator (264) may translate longitudinally to shift between a tissue clamping mode and a tissue cutting/stapling mode. For instance, driver actuator (264) may translate from a first longitudinal position, in which rotation of driver actuator (264) provides clamping of tissue at stapling head assembly (220), to a second longitudinal position, in which rotation of driver actuator (264) provides cutting and stapling of tissue at stapling head assembly (220). Some versions of shaft assembly (260) may include one or more flexible sections. An example of a shaft assembly that is configured with flexible sections and that may be incorporated into shaft assembly (260) is disclosed in U.S. patent application Ser. No. 13/716,318, entitled "Motor Driven Rotary Input Circular Stapler with Lockable Flexible Shaft,"

filed on Dec. 17, 2012 (published as U.S. Pub. No. 2014/0166728 on Jun. 19, 2014), issued as U.S. Pat. No. 9,597,081 on Mar. 21, 2017, the disclosure of which is incorporated by reference herein. Alternatively, shaft assembly (260) may be rigid along the length of shaft assembly (260) or have one or more flexible sections configured in some other fashion.

Figure 8:
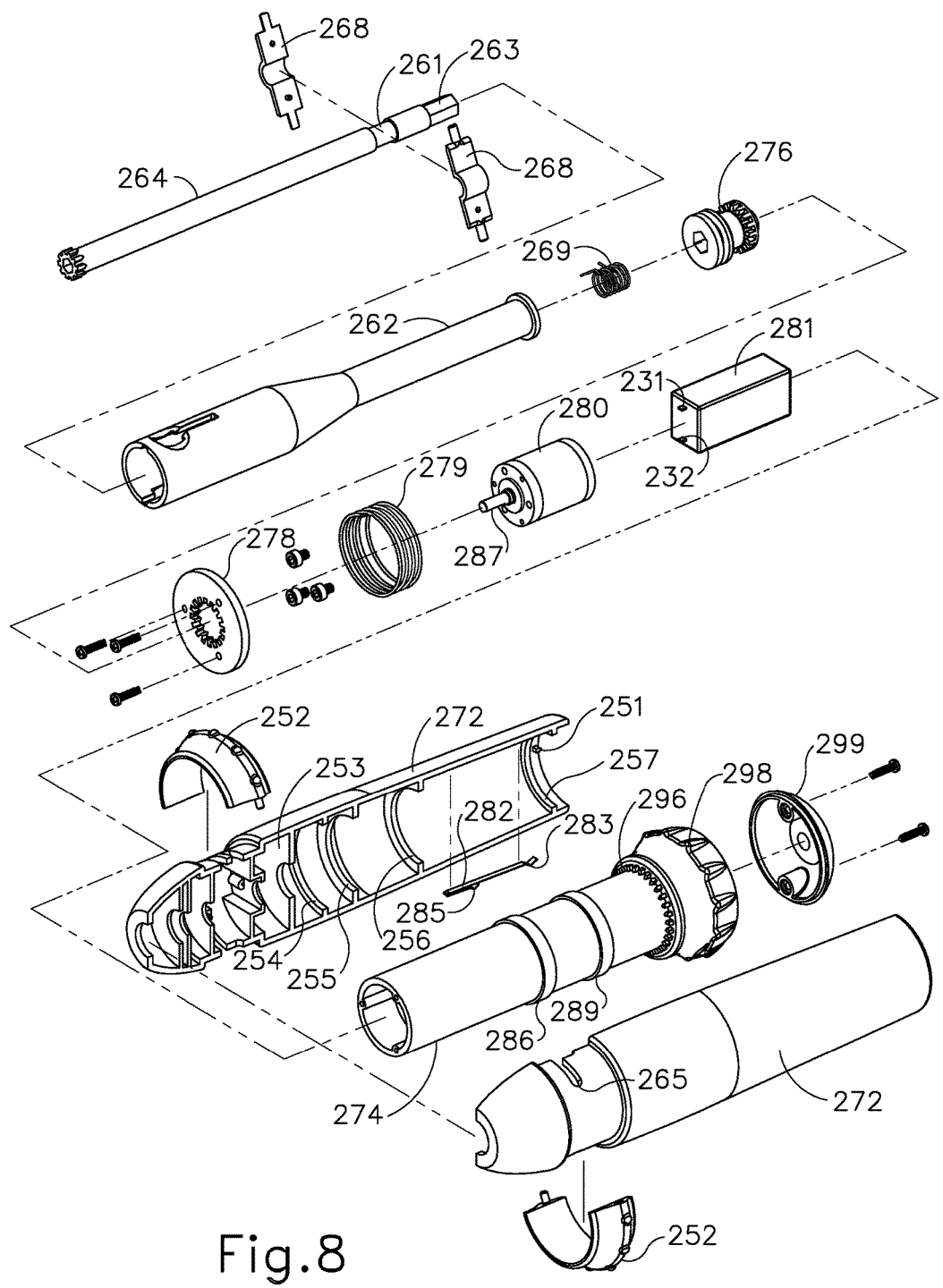
FIG. 8 depicts an exploded view of the handle and shaft assemblies of the instrument of FIG. 7.
Figure 11A:
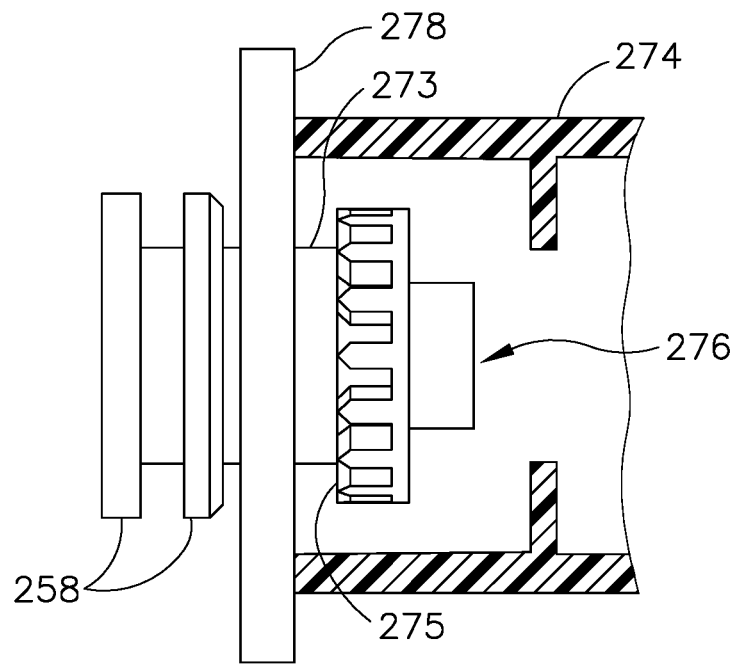
FIG. 11A depicts a side elevational view of an operational mode selection assembly of the instrument of FIG. 7, with a first gear disengaged from a second gear.
Figure 11B:
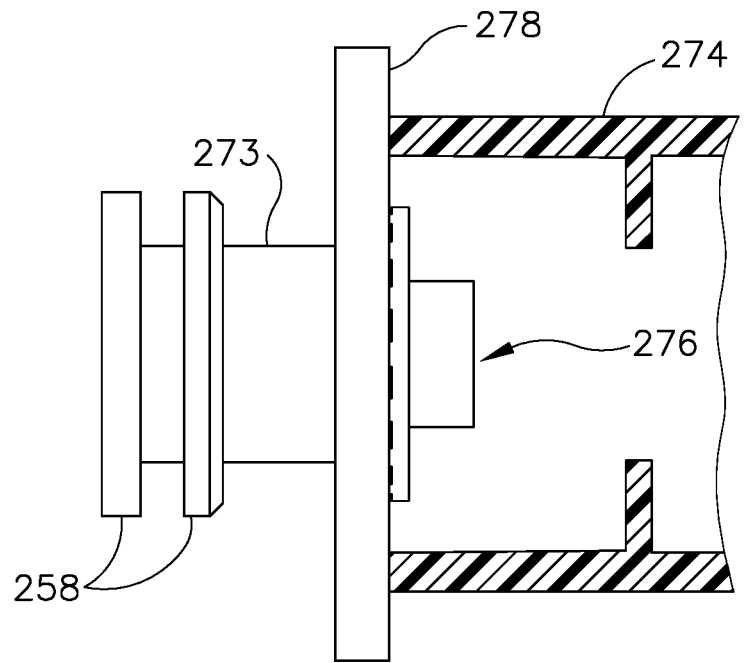
FIG. 11B depicts a side elevational view of the operational mode selection assembly of FIG. 11A, with the first gear engaged with the second gear.

Handle assembly (270) is shown in FIGS. 8-10. Handle assembly (270) comprises a handle housing (272), a motor housing (274), a motor (280), a battery (281), a rotation knob (298), an operational mode selection assembly (which is shown in FIGS. 11A-11B), and a firing ring (252). Motor housing (274) is positioned within handle housing (272). Handle housing (272) comprises ribs (255, 256, 257) extending inwardly into handle housing (272) to support motor housing (274), as shown in FIG. 9. Battery (281) is positioned proximal to motor (280) within motor housing (274). Battery (281) may be removed from motor housing (274) to be replaced, discarded, or recharged. As best seen in FIG. 10, battery (281) comprises electrical contacts (231, 232) extending distally from battery (281). Motor (280) comprises electrical contacts (233, 234) extending proximally from motor (280). Battery electrical contact (232) and motor electrical contact (234) are coupled via conductive metal band (242). Screw (243) couples band (242) to motor housing (274) to fix the position of band (242) relative to motor housing (274). Accordingly, band (242) is configured to constantly couple battery electrical contact (232) and motor electrical contact (234).

As shown in FIG. 10, battery electrical contact (231) is coupled to a conductive metal band (245). Metal band (245) is secured to motor housing (274) via a conductive screw (247). Motor electrical contact (233) is coupled to a conductive metal band (244). Metal band (244) is secured to motor housing (274) via a conductive screw (246). Motor housing (274) is formed of an electrically insulative material (e.g., plastic) and comprises annular contacts (284, 286) wrapped around motor housing (274). Screws (246, 247) are each coupled with a respective annular contact (284, 286) to electrically couple battery electrical contact (231) and motor electrical contact (233) to annular contacts (284, 286), respectively.

Another conductive metal band (282) is secured to handle housing (272). Each end of metal band (282) forms a respective spring contact (283, 285). Motor housing (274) translates proximally and/or distally relative to handle housing (272) to selectively couple and/or decouple spring contacts (283, 285) with annular contacts (284, 286). In particular, when motor housing (274) is in a distal position (FIG. 15A), spring contact (283) engages annular contact (284) and spring contact (285) engages annular contact (286) to couple battery (281) with motor (280) and supply power to motor (280). It should be understood that, since spring contacts (283, 285) are part of the same conductive metal band (282), and since contacts (232, 234) are already coupled via band (242), the engagement between spring contacts (283, 285) and annular contacts (284, 286) completes a circuit between battery (281) and motor (280). This positioning is used to provide motorized actuation of stapling head assembly (220) as will be described in greater detail below. When motor housing (274) is in a proximal position (FIG. 17A), spring contacts (283, 285) are decoupled from annular contacts (284, 286), such that battery (281) is decoupled from motor (280) and motor (280) does not receive power. This positioning is used to provide manual actuation of stapling head assembly (220) as will be described in greater detail below. The annular shape of annular contacts (284, 286) enables proper contact between spring contacts (283, 285) and annular contacts (284, 286) regardless of the angular position of motor housing (274) within handle housing (272). In some versions, band (282) may include a break that is coupled with an external switch, such that a user may actuate the external switch in order to complete the coupling between battery (281) and motor (280) after motor housing (274) is in the distal position.

A proximal end of motor housing (274) is fixedly secured to rotation knob (298), as shown in FIG. 8. Rotation knob (298) protrudes proximally from handle housing (272) and comprises splines (296) extending distally from rotation knob (298). Handle housing (272) comprises corresponding teeth (251) to selectively engage splines (296). Rotation knob (298) is pulled and/or pushed to translate motor housing (274) within handle housing (272). When rotation knob (298) is in a proximal position (FIG. 17A), splines (296) are disengaged from handle housing (272) such that rotation knob (298) and motor housing (274) are free to rotate relative to handle housing (272). This positioning is used to provide manual actuation of stapling head assembly (220) as will be described in greater detail below. When rotation knob (298) is in a distal position (FIG. 15A), splines (296) engage corresponding teeth (251) in handle housing (272) to lock rotation knob (298) and motor housing (274) from rotating relative to handle housing (272). Splines (296) and teeth (251) thus provide a mechanical ground for motor housing (274) relative to handle housing (272). This positioning is used to provide motorized actuation of stapling head assembly (220) as will be described in greater detail below. Rotation knob (298) is biased to the distal position by a resilient member (279) in handle housing (272). In particular, resilient member (279) extends distally from rib (255) of handle housing (272) to a first gear (278), which is unitarily secured to the distal end of motor housing (274). When rotation knob (298) is in the proximal position, resilient member (279) compresses between first gear (278) and rib (255) to resiliently bias handle housing (272) to the distal position.

Figure 12:
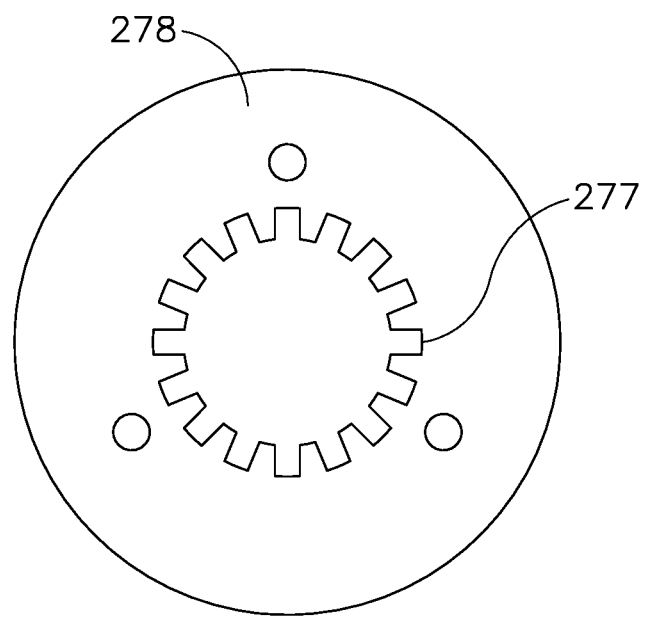
FIG. 12 depicts a front elevational view of the first gear of the operational mode selection assembly of FIG. 11A.
Figure 13:
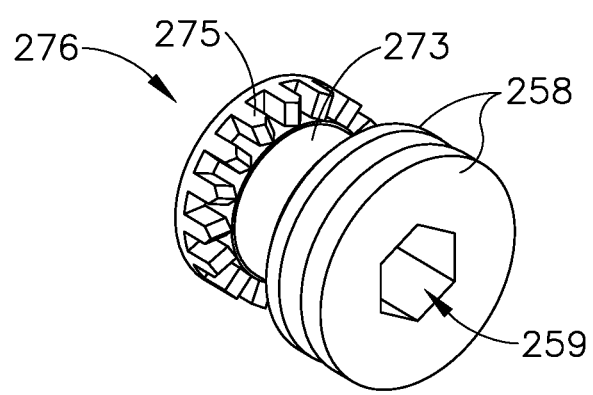
FIG. 13 depicts a perspective view of the second gear of the operational mode selection assembly of FIG. 11A.

An operational mode selection assembly is positioned distal to motor housing (274) within handle housing (272). As shown in FIGS. 11-13, the operational mode selection assembly comprises a first gear (278) and a second gear (276), with first gear (278) being coaxially and slidably disposed about second gear (276). First gear (278) comprises square teeth (277) aligned around an inner opening of first gear (278), as shown in FIG. 12. Teeth (277) define a circumferentially spaced array of recesses. Second gear (276) comprises a shaft (273), splines (275), and annular flanges (258), as shown in FIG. 13. Shaft (273) has a distally presented opening (259). Distally presented opening (259) is hexagonal to receive proximal end (263) of driver actuator (264), which is also hexagonal (FIG. 8). Shaft (273) also has a proximally presented opening (not shown) that is semi-circular to complement and receive drive shaft (287) extending distally from motor (280). Other suitable shapes and configurations of shafts (263, 287) may used to couple second gear (276) with shafts (263, 287).

Splines (275) of second gear (276) are positioned on a proximal end of shaft (273) and extend distally. Splines (275) correspond to teeth (277) of first gear (278), such that splines (275) are configured to fit within the recesses defined between teeth (277). A pair of annular flanges (258) are positioned at a distal end of shaft (273) and extend outwardly to engage an inwardly extending annular rib (253) of handle housing (272), thereby fixing the longitudinal position of second gear (276) within handle housing (272). While annular rib (253) fixes the longitudinal position of second gear (276) within handle housing (272), annular rib (253) nevertheless allows second gear (276) to rotate relative to handle housing (272). Other suitable engagement features to longitudinally fix second gear (276) will be apparent to one with ordinary skill in the art based on the teachings herein.

Figure 17A:
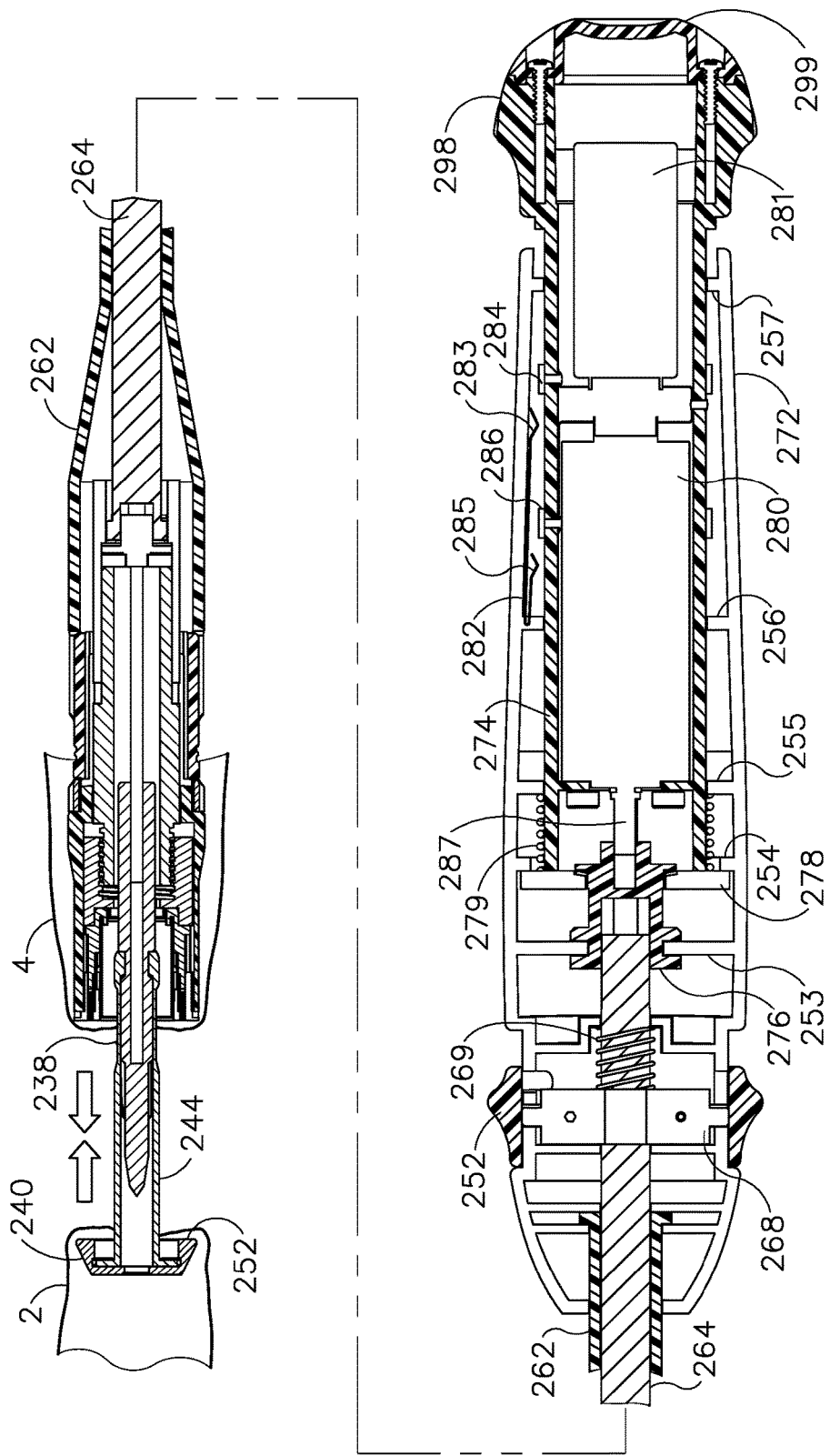
FIG. 17A depicts a cross sectional view of the instrument of FIG. 7, with a manual operational mode selected, showing an anvil being coupled to a trocar.

First gear (278) is positioned around second gear (276), as shown in FIGS. 11A-11B. First gear (278) is fixedly coupled to a distal end of motor housing (274) such that first gear (278) translates and rotates unitarily with motor housing (274). When motor housing (274) is in a proximal position, as shown in FIGS. 11B and 17A, motor (280) and first gear (278) are also in a proximal position. In this position, drive shaft (287) of motor (280) is disengaged from second gear (276) and teeth (277) of first gear (278) engage splines (275) of second gear (276). Thus, when rotation knob (298) rotates, motor housing (274) and first gear (278) also rotate. This positioning thereby provides manual actuation of stapling head assembly (220), as will be described in greater detail below. With teeth (277) of first gear (278) engaged with splines (275), rotation knob (298) thereby rotates second gear (276) relative to motor housing (274). When motor housing (274) is in a distal position, as shown in FIGS. 11A and 15B, motor (280) and first gear (278) are also in a distal position. Motor (280) is engaged with second gear (276) via shafts (287, 273). First gear (278) slides over shaft (273) of second gear (276) to disengage splines (275). Thus, the rotation of drive shaft (287) of motor (280) thereby rotates second gear (276). This positioning thereby provides motorized actuation of stapling head assembly (220), as will be described in greater detail below. In other words, when knob (298) and motor housing (274) are in a distal position as shown in FIGS. 11A and 15B, motor (280) rotates second gear (276). When knob (298) and motor housing (274) are in a proximal position as shown in FIGS. 11B and 17A, knob (298) rotates second gear (276).

Figure 14:
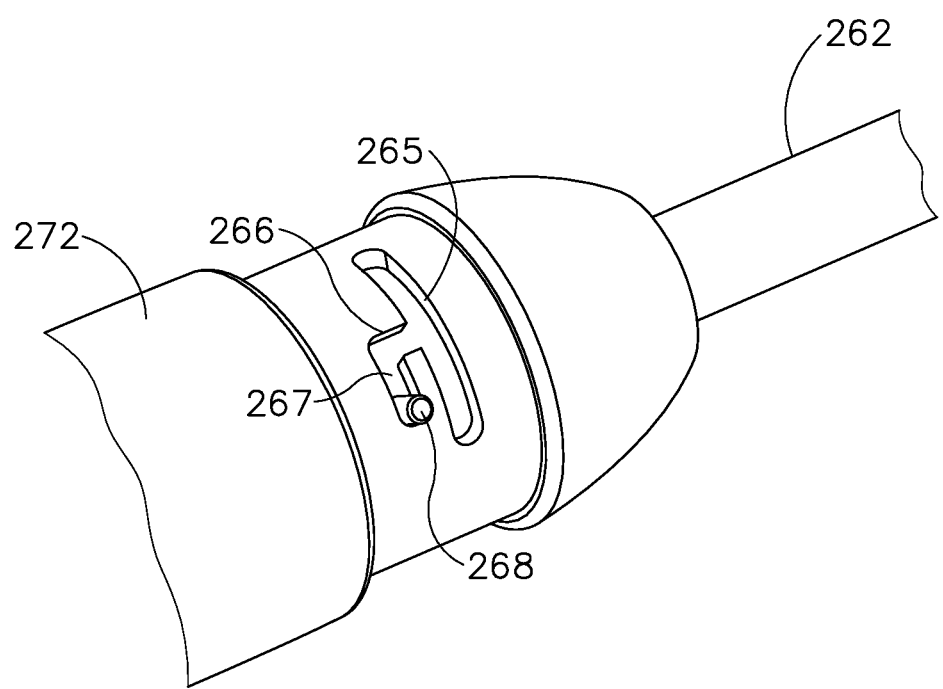
FIG. 14 depicts an enlarged, partial perspective view of the handle assembly of the instrument of FIG. 7.

Referring back to FIGS. 8-9, a distal end of second gear (276) is coupled to driver actuator (264), such that rotation of second gear (276) rotates driver actuator (264). Driver actuator (264) is similar to driver actuator (64). Accordingly, when second gear (276) is rotated, driver actuator (264) is rotated to adjust the gap distance d between anvil (240) and stapling head assembly (220). Handle housing (272) further comprises firing ring (252) and coupling member (268). Coupling member (268) is secured around recess (261) of driver actuator (264), as shown in FIG. 8. Accordingly, coupling member (268) translates with driver actuator (264), but driver actuator (264) is free to rotate within coupling member (268). Coupling member (268) comprises protrusions extending outwardly that connect coupling member (268) to firing ring (252). The protrusions of coupling member (268) extend through slots (265, 266, 267) of housing assembly (272), as shown in FIG. 14. Slot (265) extends circumferentially about part of handle assembly (272). Slot (266) extends proximally from slot (265). Slot (267) extends transversely from slot (266) and is substantially parallel with slot (265). Firing ring (252) is wrapped around handle housing (272) and is rotatable and translatable relative to handle housing (272) to manually drive the protrusions of coupling member (268) through slots (265, 266, 267).

When firing ring (252) is in a distal position, protrusions of coupling member (268) are positioned within slot (265) of handle housing (272). When coupling member (268) is positioned within slot (265), coupling member (268) couples driver actuator (264) with features in stapling head assembly (220) operable to adjust the gap distance d between anvil (240) and stapling head assembly (220). For instance, if coupling member (268) is rotated clockwise within slot (265), the gap distance d is decreased to close anvil (240) relative to stapling head assembly (220). If coupling member (268) is rotated counterclockwise within slot (265), the gap distance d is increased to open anvil (240) relative to stapling head assembly (220). A resilient member (269) is positioned proximal to coupling member (268) to bias coupling member (268) distally (FIG. 8). Coupling member (268) of firing ring (252) may then be translated proximally through slot (266) to slot (267). When firing ring (252) is in the proximal position, protrusions of coupling member (268) are positioned within slot (267). When coupling member (268) is positioned within slot (267), coupling member (268) couples driver actuator (264) with features in stapling head assembly (220) that drive knife (36) and staples (66) in response to rotation of driver actuator (264). For instance, if coupling member (268) is rotated clockwise within slot (267), stapling head assembly (220) drives knife (36) and staples (66). The configuration of slot (367) prevents coupling member (268) from being rotated counterclockwise. Other suitable coupling member (268) rotation configurations will be apparent to one with ordinary skill in view of the teachings herein.

As shown in FIG. 9, a switch (248) is positioned in handle housing (272) to align with coupling member (268). When the motorized operational mode is selected, switch (248) is configured to electrically couple motor (280) and battery (281) when switch (248) is depressed, and switch (248) is configured to electrically decouple motor (280) and battery (281) when switch (248) is not depressed. Coupling member (268) is configured to engage and depress switch (248) when coupling member (268) is rotated. For instance, when coupling member (268) is in a neutral position (e.g., when coupling members (268) are aligned with respective slots (266)), switch (248) is not depressed and motor (280) is decoupled from battery (281). When coupling member (268) is rotated away from the neutral position, coupling member (268) engages switch (248) to depress switch (248) and couple motor (280) with battery (281) to operate instrument (210). It should be understood that housing (272) may include three switches (248). For instance, one switch (248) may be positioned for activation when firing ring (252) is rotated clockwise while in the proximal position (e.g., with coupling member (268) in slot (267)); with another switch (248) being positioned for activation when firing ring (252) is rotated clockwise while in the distal position (e.g., with coupling member (268) in slot (265)); with yet another switch (248) being positioned for activation when firing ring (252) is rotated counterclockwise while in the distal position. A control logic may be in communication with the switches (248) that are activated when firing ring (252) is rotated while in the distal position. Such a control logic may be operable to selectively reverse the direction of rotation by motor (280), to thereby provide selective advancement or retraction of trocar (238) and anvil (240) to adjust the gap distance d, depending on the direction in which firing ring (252) is rotated.

It should be understood that firing ring (252) and coupling member (268) act as a clutch control to shift driver actuator (264) from an anvil clamping mode (when coupling member (268) is in the distal position) to a cutting/stapling mode (when coupling member (268) is in the proximal position). An example of a stapling head assembly (220) responsive to such changes in driver actuator (264) positioning is disclosed in U.S. patent application Ser. No. 13/716,318, entitled "Motor Driven Rotary Input Circular Stapler with Modular End Effector," filed on Dec. 17, 2012 (published as U.S. Pub. No. 2014/0166728 on Jun. 19, 2014), issued as U.S. Pat. No. 9,597,081 on Mar. 21, 2017, the disclosure of which is incorporated by reference herein. Other suitable forms that stapling head assembly (220) may take will be apparent to those of ordinary skill in the art in view of the teachings herein. Outer tubular member (262) is coupled to actuator handle assembly (270). Outer tubular member (262) is similar to outer tubular member (62) to provide a mechanical ground between stapling head assembly (220) and handle assembly (270).

1. Motorized Operation

Figure 15A:
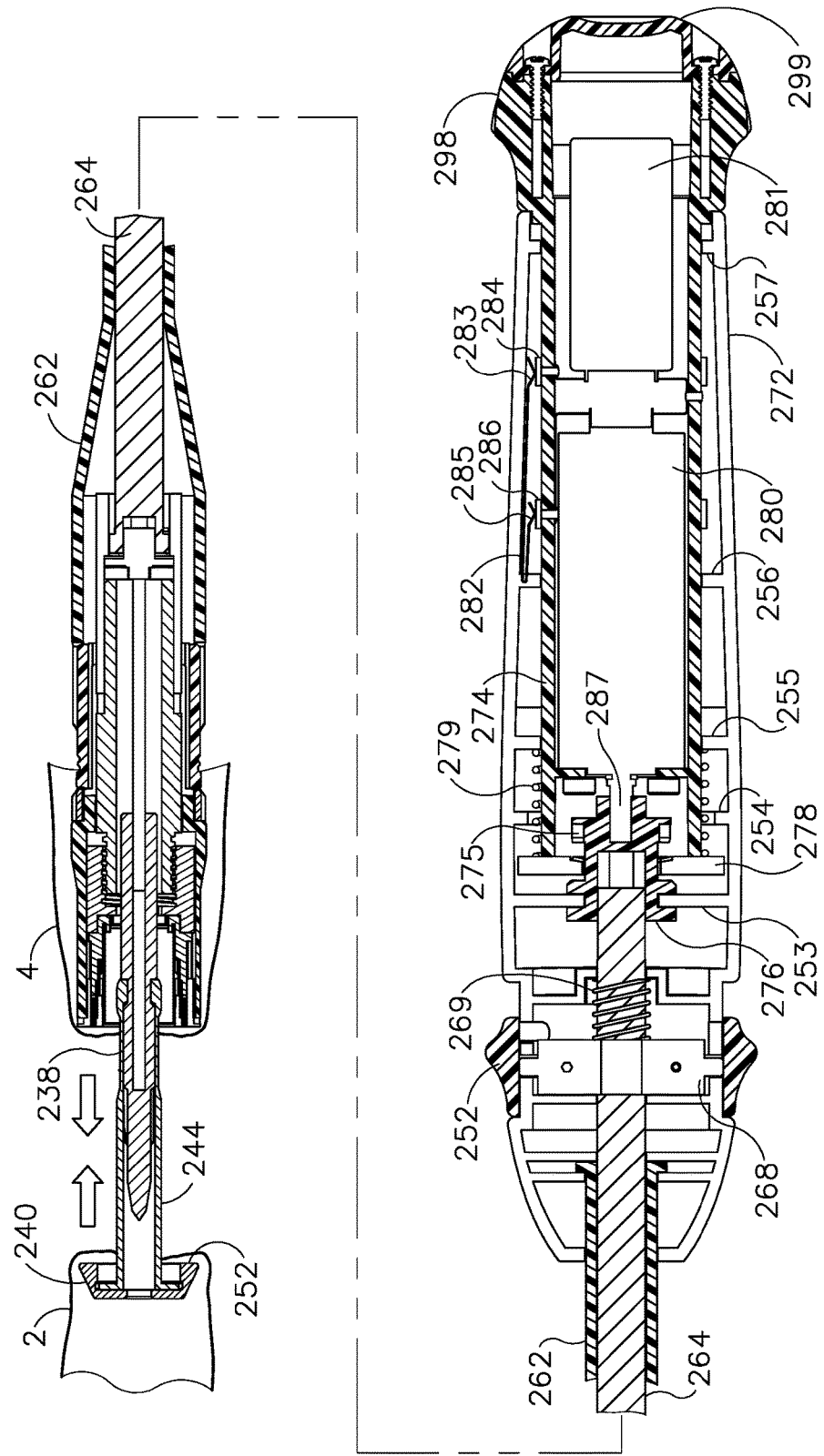
FIG. 15A depicts a cross sectional view of the instrument of FIG. 7, with a motorized operational mode selected, showing an anvil being coupled to a trocar.
Figure 15B:
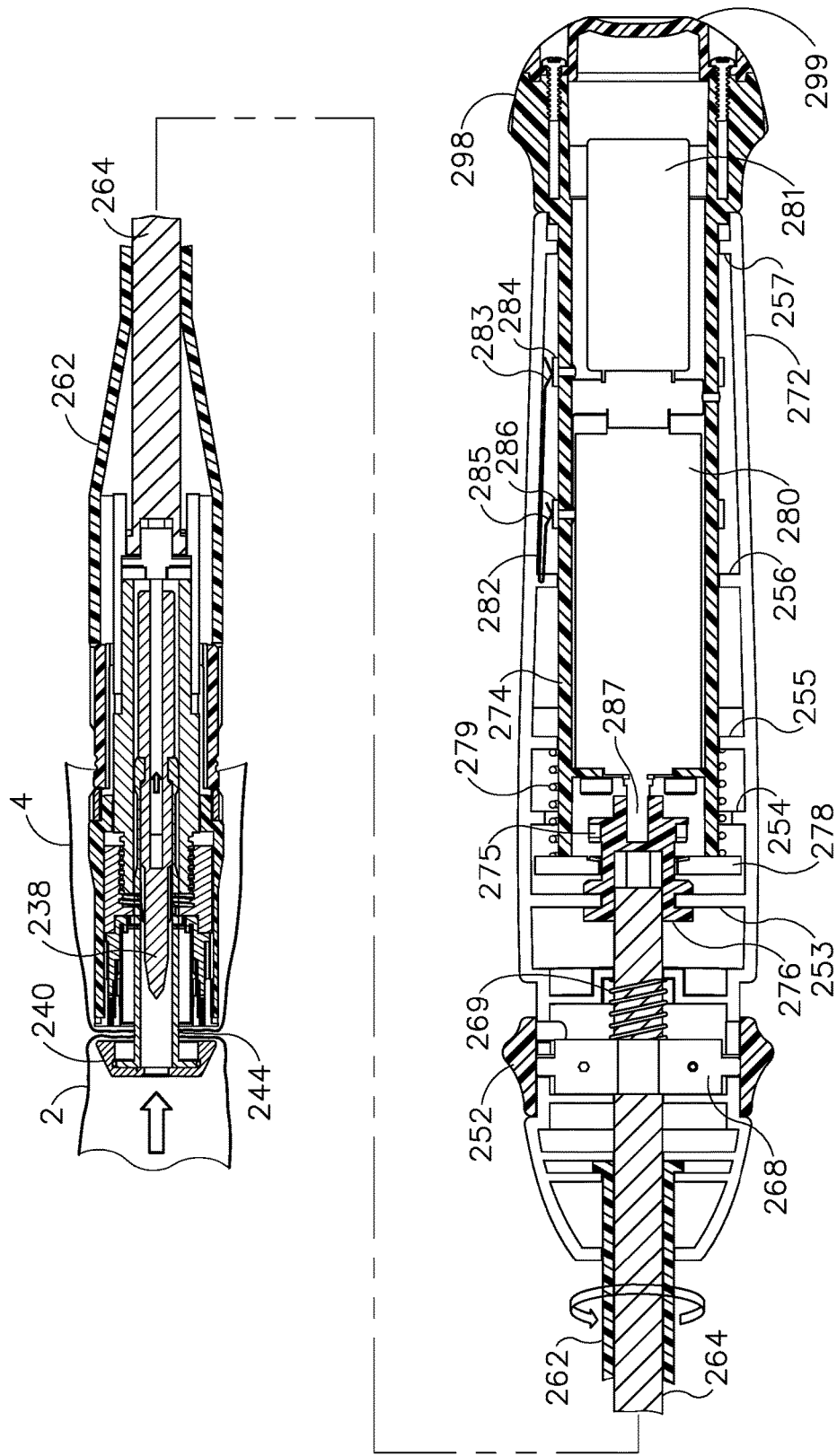
FIG. 15B depicts a cross sectional view of the instrument of FIG. 7, with a motorized operational mode selected, in a tissue clamping position.
Figure 15C:
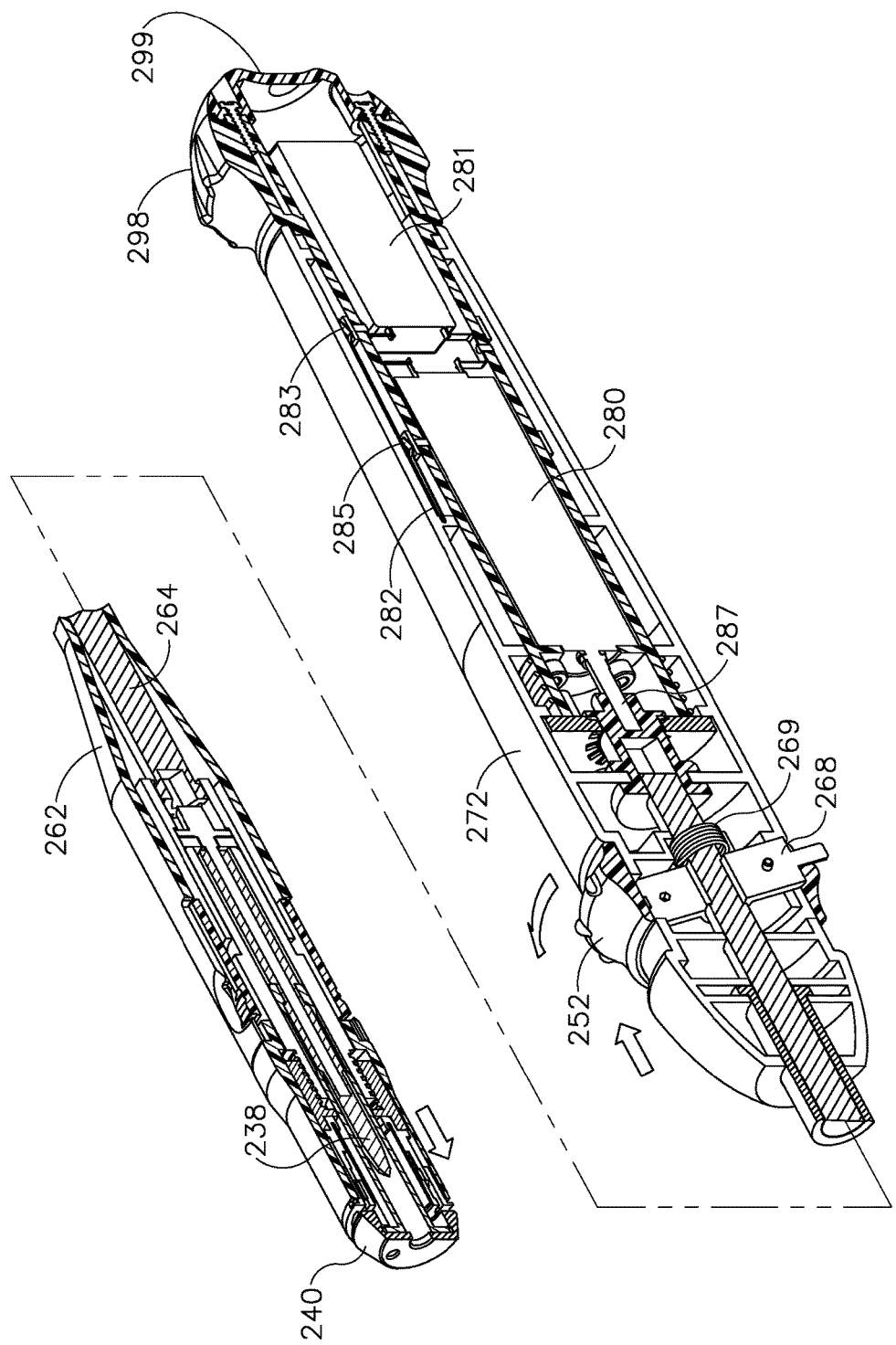
FIG. 15C depicts a cross sectional view of the instrument of FIG. 7, with a motorized operational mode selected, in a fired position.

FIGS. 15A-15C show instrument (210) during motorized operation. FIG. 15A shows anvil (240) being coupled to trocar (238). Anvil (240) couples with trocar (238) in a manner similar to that described above with respect to anvil (40) and trocar (38). When motorized operation is selected, rotation knob (298) is in a distal position. In the distal position, splines (296) of rotation knob (298) engage corresponding teeth (251) in handle housing (272) to lock rotation knob (298) from rotating relative to handle housing (272). When rotation knob (298) is in the distal position, motor housing (274) is also in a distal position. When motor housing (274) is in the distal position, spring contacts (283, 285) are aligned with annular contacts (284, 286) to couple electrical contact (231) of battery (281) with electrical contact (233) of motor (280). Power is supplied from battery (281) to motor (280) when coupling member (268) is rotated to depress switch (248). Motor (280) is engaged with second gear (276) via shafts (287, 273) and first gear (278) is disengaged from splines (275), thereby permitting second gear (276) to rotate relative to first gear (278), motor housing (274), and handle housing (272). Protrusions of coupling member (268) are positioned distally within slot (265) of handle housing (272) to lock the longitudinal position of firing ring (252) and driver actuator (264).

As shown in FIG. 15B, firing ring (252) is rotated clockwise to translate coupling member (268) within slot (267). As coupling member (268) is rotated, switch (248) is depressed to couple motor (280) and battery (281) and supply power to motor (280). Motor (280) is thus activated to rotate shaft (287). Shaft (287) thereby rotates second gear (276). Because second gear (276) is coupled to driver actuator (264), the rotation of second gear (276) also rotates driver actuator (264). This rotation of driver actuator (264) drives features in stapling head assembly (220) to adjust the gap distance d between anvil (240) and stapling head assembly (220). Once anvil (240) is in a desired position relative to stapling head assembly (220), firing ring (252) is rotated counterclockwise to a neutral position to release switch (248) such that motor (280) is decoupled from battery (281). Instrument (210) may then be fired, as shown in FIG. 15C. Firing ring (252) is translated to position coupling member (268) out of slot (265) to the proximal position in slot (267). When coupling member (268) is translated proximally to slot (267), coupling member (268) also translates driver actuator (264) proximally to couple driver actuator (264) with features in stapling head assembly (220) operable to drive knife (36) distally and to drive staples (66) into anvil (240) to staple the clamped tissue (2, 4) to create an anastomosis. Firing ring (252) is rotated clockwise within slot (267) to depress switch (248) to again couple battery (281) with motor (280) to supply power to motor (280). Motor (280) is again rotated with coupling member (268) and driver actuator (264) in the proximal position. This rotation is communicated to driver actuator (264) via drive shaft (287) and second gear (276), and is thereby communicated to driver actuator (264) to cut and staple tissue (2, 4). Firing ring (252) may then be rotated counterclockwise within slot (267) to the neutral position to release switch (248) and decouple motor (280) from battery (281).

2. Selection of Operation Mode

Figure 16:
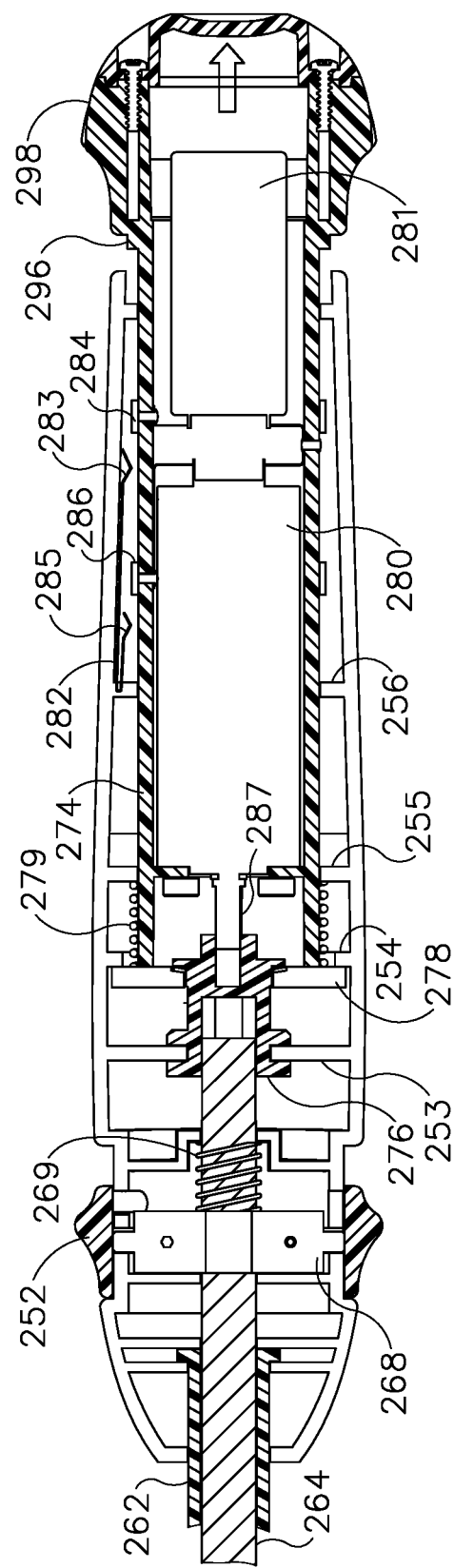
FIG. 16 depicts a cross sectional view of the handle assembly of the instrument of FIG. 7 showing the manual operational mode being selected.

As shown in FIG. 16, instrument (210) is switched from motorized operation to manual operation. A user may grasp rotation knob (298) to translate rotation knob (298) from the distal position to the proximal position. In the proximal position, splines (296) of rotation knob (298) disengage from corresponding teeth (251) in handle housing (272) to allow rotation knob (298) to rotate relative to handle housing (272). This also allows motor housing (274) and first gear (278) to rotate relative to handle housing (272). When rotation knob (298) is in the proximal position, motor housing (274) is also in a proximal position. When motor housing (274) is in the proximal position, spring contacts (283, 285) are offset from annular contacts (284, 286) to decouple battery (281) from motor (280) such that no power is supplied to motor (280). First gear (278) translates proximally to engage splines (275) of second gear (276). Thereby, rotation of rotation knob (298) rotates motor housing (274), first gear (278), second gear (276), and driver actuator (264). A user may also push rotation knob (298) back distally to reselect motorized operation. By using rotation knob (298) as an actuator to select between motorized and manual operation, the need for lockouts or switches to simultaneously remove power to motor (280) is eliminated. Rotation knob (298) thus provides a "bailout" system of motorized operation, while allowing instrument (210) to be fully operational in the manual operational mode. It should therefore be understood that even if an operator initially uses instrument (210) in a motorized mode, the operator may quickly and easily convert instrument (210) to a manually operated mode simply by pulling on rotation knob (298), without sacrificing essential functionality of instrument (210).

3. Manual Operation

Figure 17B:
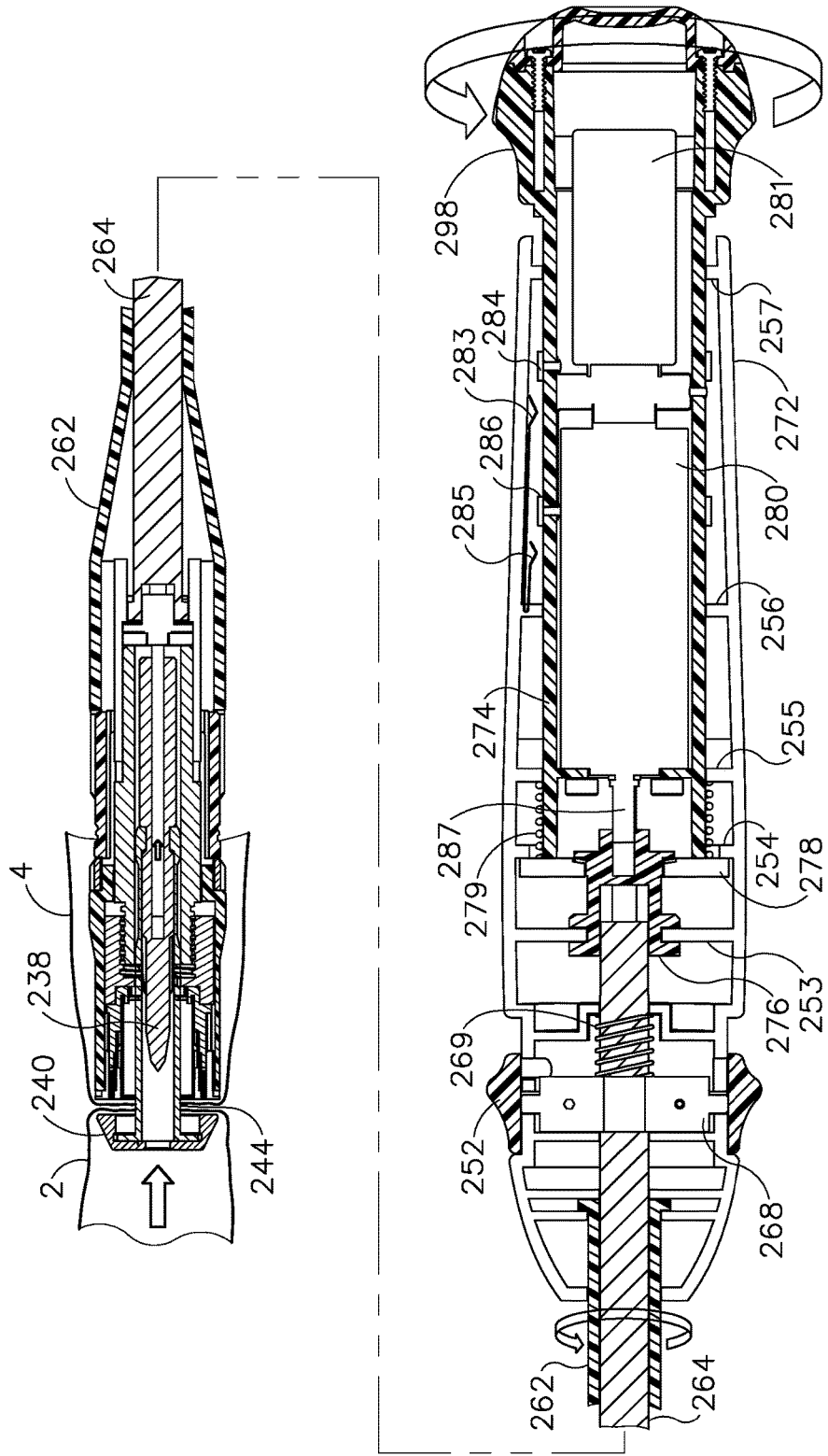
FIG. 17B depicts a cross sectional view of the instrument of FIG. 7, with a manual operational mode selected, in a tissue clamping position.
Figure 17C:
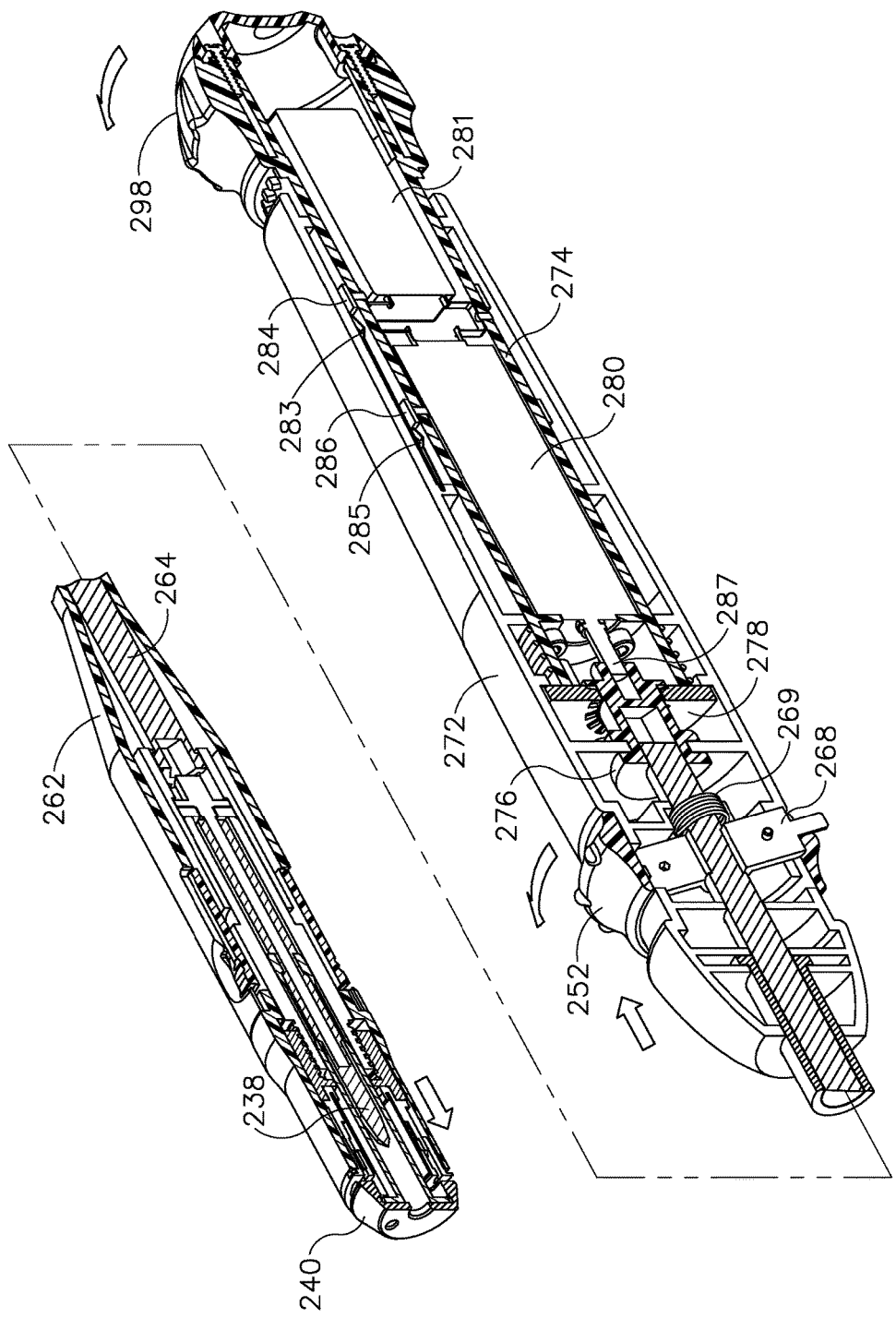
FIG. 17C depicts a cross sectional view of the instrument of FIG. 7, with a manual operational mode selected, in a fired position.

FIGS. 17A-17C show instrument (210) during manual operation. FIG. 17A shows anvil (240) being coupled to trocar (238). Rotation knob (298) is in the proximal position, as described above. As shown in FIG. 17B, rotation knob (298) is rotated to rotate motor housing (274) relative to handle housing (272). Motor housing (274) thereby rotates first gear (278). First gear (278) is engaged with splines (275) to rotate second gear (276). Because second gear (276) is coupled to driver actuator (264), the rotation of second gear (276) also rotates driver actuator (264). This rotation of driver actuator (264) rotates features in stapling head assembly (220) to adjust the gap distance d between anvil (240) and stapling head assembly (220). Once anvil (240) is in a desired position relative to stapling head assembly (220), instrument (210) may be fired, as shown in FIG. 17C. Firing ring (252) is translated from the distal position and out of slot (265) to the proximal position with slot (267). When coupling member (268) is translated proximally to slot (267), coupling member (268) also translates driver actuator (264) proximally to couple driver actuator (264) with features in stapling head assembly (220) operable to drive knife (36) distally and to drive staples (66) into anvil (240) to staple the clamped tissue (2, 4) to create an anastomosis. Rotation knob (298) is again rotated with coupling member (268) and driver actuator (264) in the proximal position. This rotation is communicated to driver actuator (264) via first gear (278) and second gear (276), and is thereby communicated to driver actuator (264) to cut and staple tissue (2, 4).

4. Control Assembly

Figure 18:
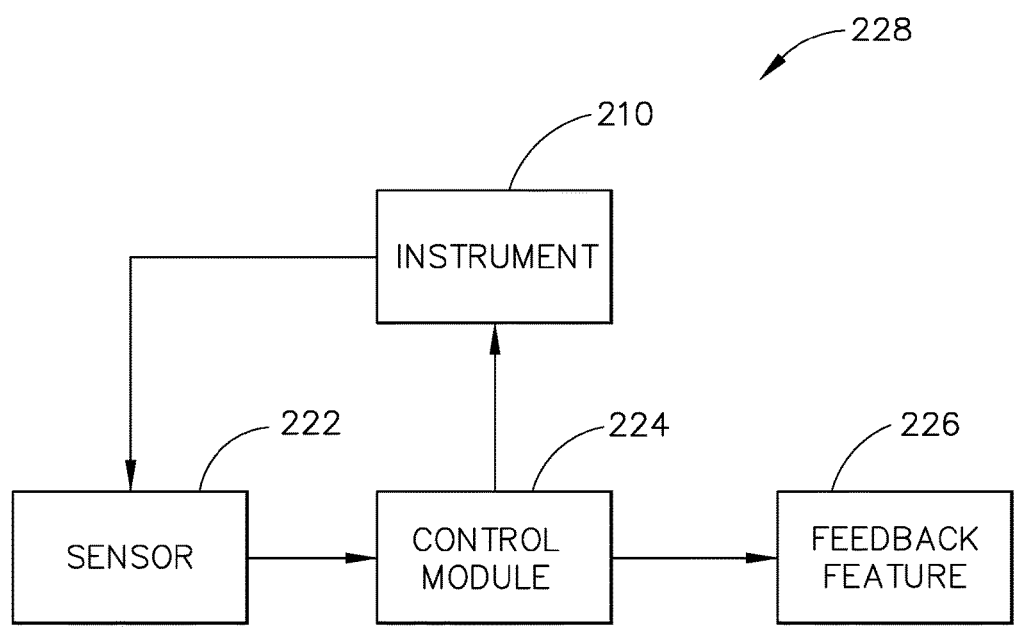
FIG. 18 depicts a schematic of an exemplary control assembly for use with the instrument of FIG. 7.

FIG. 18 shows an exemplary control assembly (228) for use with instrument (210). Control assembly (228) comprises a sensor (222), a control module (224), and a feedback feature (226). Feedback feature (226) may be operable to provide visual, audio, and/or haptic feedback (LED lights, LED display, speaker, vibration generator, etc.). Sensor (222) is coupled to instrument (210) and is configured to detect movement within the drive train of instrument (210). For example, sensor (222) may comprise an encoder positioned to detect rotation of driver actuator (264) or some other rotating component of drive train (e.g, a component that rotates but does not also translate). Sensor (222) is coupled with control module (224) to provide the sensed signal to control module (224). Control module (224) is configured to process the sensed signal and may determine the selected operational mode of instrument (210), the gap distance d between anvil (240) and stapling head assembly (220), and/or the firing of knife (36) and staples (66). In the present example, control module (224) is coupled with instrument (210) and feedback feature (226). However, control module (224) may be coupled with either of instrument (210) or feedback feature (226). Control module (224) may also be coupled with switch (248) to actuate motor (280) when switch (248) is depressed. Each of sensor (222), control module (224), and feedback feature (226) may be located within instrument (210) or remotely from instrument (210).

Based on the sensed signal, control module (224) is operable to actuate instrument (210) and/or feedback feature (226). For example, control module (224) may actuate feedback feature (226) to indicate the selected operational mode of instrument (210). In some versions, feedback feature (226) may have a first LED corresponding to the motorized operational mode and a second LED corresponding to the manual operational mode. Sensor (222) may detect the proximal and/or distal position of rotation knob (298) and/or motor housing (274) and provide the information to control module (224). Control module (224) may then illuminate the first LED if sensor (222) detects the proximal position to indicate the motorized operational mode is selected. Control module (224) may illuminate the second LED if sensor (222) detects the distal position to indicate the manual operational mode is selected. Alternatively, feedback feature (226) may have only one LED which is either illuminated or not to indicate the operational mode, or feedback feature (226) may have a speaker to provide a sound when the operational mode is changed.

In some versions, control module (224) may actuate feedback feature (226) to indicate the selected mode of stapling assembly (220). Feedback feature (226) may have a first LED corresponding to the tissue clamping mode and a second LED corresponding to the firing mode. Sensor (222) may detect the proximal and/or distal position of firing ring (252), coupling member (268) and/or driver actuator (264) and provide the information to control module (224). Control module (224) may then illuminate the first LED if sensor (222) detects the distal position to indicate the tissue clamping mode is selected. Control module (224) may illuminate the second LED if sensor (222) detects the proximal position to indicate the firing mode is selected. Alternatively, feedback feature (226) may have only one LED which is either illuminated or not to indicate stapling head assembly (220) mode, or feedback feature (226) may have a speaker to provide a sound when stapling head assembly (220) mode is changed.

In addition or in the alternative, control module (224) may actuate feedback feature (226) to indicate the gap distance d between anvil (240) and stapling head assembly (220). Sensor (222) may detect the number of rotations of driver actuator (264). Control module (224) may then determine the gap distance d based on the sensed signal and actuate feedback feature (226). Feedback feature (226) may comprise a plurality of LEDs that individually illuminate to indicate the gap distance d. As gap distance d increases, LEDs may illuminate to correspond to the gap distance d. As gap distance d decreases, LEDs may turn off to correspond to the gap distance d. As another merely illustrative example, feedback feature (226) may comprise an LED display screen that provides a real-time indication of the gap distance d. Feedback feature (226) may also have a speaker that emits a sound that changes in either pitch or volume to indicate the corresponding gap distance d. Alternatively, one LED may be used to indicate when a particular gap distance d has been reached, or a sound may be provided when the particular gap distance d has been reached.

In versions where feedback feature (226) includes the capability of providing haptic feedback to the operator, it should be understood that various conventional components may be incorporated into handle assembly (270) to provide such haptic feedback. It should also be understood that haptic feedback may be provided through motor (280). By way of example only, feedback feature (226) may be configured to provide a sine wave signal to motor (280) to essentially rotate drive shaft (287) slightly clockwise and then immediately rotating it slightly counterclockwise the exact same amount. The net result would be zero rotational displacement of drive shaft (287). When this sequence is repeated (e.g., in a rapid succession), the movement of drive shaft (287) may cause handle assembly (270) to vibrate or otherwise shake enough for the operator to feel it through the hand that grasps handle assembly (270). With the zero net movement of drive shaft (287) through this feedback algorithm, the haptic feedback may result in no net actuation of anything in head assembly (220), regardless of whether driver actuator (264) is in the distal position or the proximal position. Such haptic feedback may be provided to indicate the end of a stapling stroke, to indicate a lockout condition, and/or to indicate some other condition. Various other suitable ways in which audio, visual, and/or haptic feedback may be provided will be apparent to those of ordinary skill in the art in view of the teachings herein.

In some versions, control module (224) may actuate instrument (210). Sensor (222) may be configured to detect when knife (36) and staples (66) have been fired. Control module (224) may thus automatically reverse motor (280) once knife (36) and staples (66) have been fired. Control module (224) may also actuate feedback feature (226) to indicate to a user that instrument (210) has been fired. Other suitable ways in which sensors (222), control module (224), and feedback feature (226) may be used will be apparent to those of ordinary skill in the art in view of the teachings herein. It should also be understood that such features may be simply omitted if desired.

B. Exemplary Switch Assembly

Figure 19:
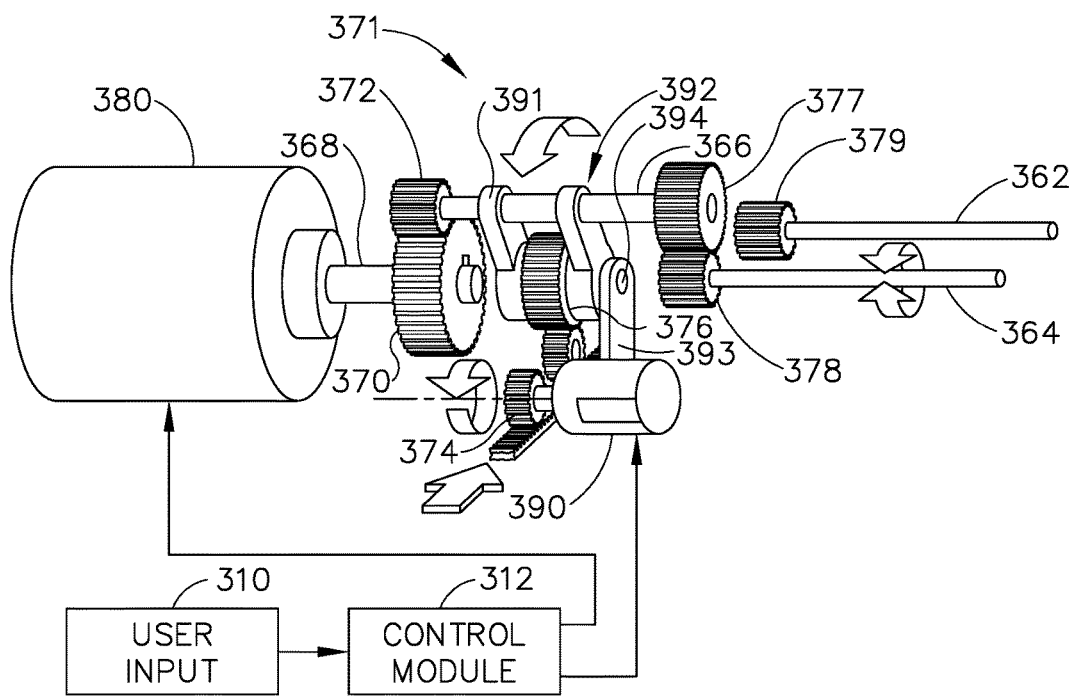
FIG. 19 depicts a partial perspective view of another exemplary operational mode selection assembly.
Figure 20:
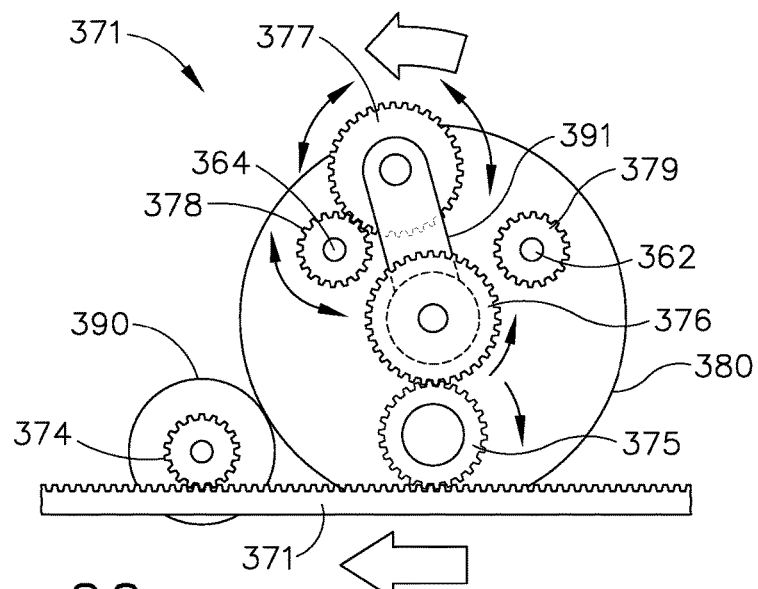
FIG. 20 depicts a front view of the operational mode selection assembly of FIG. 19.

As described above, surgical stapling instrument (10, 210) has two sub-systems, a closure sub-system (to clamp tissue between anvil (40, 240) and stapling head assembly (20, 220)) and a firing sub-system (to drive knife (36) and staples (66) distally toward anvil (40, 240)), in order to create an anastomosis. It may be desirable to power both sub-systems with a single rotary motor to eliminate the cost and packaging of an additional motor and transmission. FIGS. 19-20 show an exemplary drive assembly (371) configured to power two sub-systems with a single rotary motor (380). While instrument (210) provided closure and firing with a single rotary drive shaft, drive assembly (371) of this example provides closure and firing through two separate rotary drive shafts driven by a single motor (380). Drive assembly (371) comprises a motor (380), a transmission shaft (392), a solenoid (390), a closure rod (364), and a firing rod (362). Motor (380) comprises a shaft (368) extending from motor (380) and a gear (370) coupled to shaft (368). Transmission shaft (392) comprises a gear (372) engaged with gear (370) of motor (380). A gear (377) is positioned on the opposing end of transmission shaft (392).

A pivoting swing arm (391) is wrapped around transmission shaft (392) such that transmission shaft (392) may freely rotate relative to swing arm (391), as shown in FIG. 18. Swing arm (391) extends from transmission shaft (392) and comprises a gear (376). Gear (376) is fixedly secured to swing arm (391). A pin (394) extends from swing arm (391) and is coaxial with gear (376). Pin (394) is pivotally supported by a bracket (393), such that swing arm (391) is pivotable about pin (394) relative to bracket (393) in response to rotation of gear (376). Solenoid (390) comprises a gear (374) coupled to a rack (371). Rack (371) is also coupled to a gear (375), which engages gear (376) of swing arm (391). Alternatively, gear (374) of solenoid (390) may directly couple to gear (376) of swing arm (391). Closure rod (364) comprises a gear (378). Firing rod (362) is positioned adjacent to and substantially parallel with closure rod (364). Firing rod (362) comprises a gear (379). Gear (377) of transmission shaft (392) selectively swings to engage either gear (378) of closure rod (364) or gear (379) of firing rod (362).

As shown in FIGS. 19-20, transmission shaft (392) is positioned to engage closure rod (364). Accordingly, when motor (380) is activated, shaft (368) rotates gear (370). Gear (370) thereby rotates gear (372) and transmission shaft (392) to rotate gear (377). Because gear (377) is engaged with gear (378), transmission shaft (392) thereby rotates closure rod (364). Closure rod (364) may be used to adjust the gap distance d between anvil (40, 240) and stapling head assembly (20, 220). If a user desires to switch to the firing sub-system, solenoid (390) may be actuated. When solenoid (390) is actuated, solenoid (390) rotates gear (374) to translate rack (371). Rack (371) then rotates gear (375) and gear (376) of swing arm (391). Gear (376) thereby pivots swing arm (391). As swing arm (391) pivots, swing arm (391) translates transmission shaft (392) such that transmission shaft (392) disengages closure rod (364) and engages firing rod (362). Accordingly, when motor (380) is activated, shaft (368) rotates gear (370). Gear (370) thereby rotates gear (372) and transmission shaft (392) to rotate gear (377). Because gear (377) is now engaged with gear (379), transmission shaft (392) thereby rotates firing rod (362). Firing rod (364) may be used to drive knife (36) and staples (66) distally toward anvil (40, 240). Solenoid (390) may then be actuated again such that switch assembly (371) switches to the closure sub-system via swing arm (391).

Solenoid (390) may be button activated or be otherwise manually activated. Alternatively, switching assembly (371) may incorporate logic such that solenoid (390) is activated automatically. For instance, a user may actuate drive assembly (371) by inputting a user input (310) into a control module (312), as shown in FIG. 19. Control module (312) is coupled to motor (380) and solenoid (390) to selectively actuate motor (380) and/or solenoid (390) based on user input (310). Control module (312) may be integral with instrument (10, 210), or control module (312) may be a separate assembly. Suitable control module (312) configurations will be apparent to one with ordinary skill in the art in view of the teachings herein.

III. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

At least some of the teachings herein may be readily combined with one or more teachings of U.S. Pat. No. 7,794,475, entitled "Surgical Staples Having Compressible or Crushable Members for Securing Tissue Therein and Stapling Instruments for Deploying the Same," issued Sep. 14, 2010, the disclosure of which is incorporated by reference herein. Various suitable ways in which such teachings may be combined will be apparent to those of ordinary skill in the art.

Similarly, at least some of the teachings herein may be readily combined with one or more teachings of U.S. patent application Ser. No. 13/693,430, entitled "Trans-Oral Circular Anvil Introduction System with Dilation Feature," filed Dec. 4, 2012, issued as U.S. Pat. No. 9,572,573 on Feb. 21, 2017, the disclosure of which is incorporated by reference herein. Various suitable ways in which such teachings may be combined will be apparent to those of ordinary skill in the art.

Similarly, at least some of the teachings herein may be readily combined with one or more teachings of U.S. patent application Ser. No. 13/688,951, entitled "Surgical Staple with Integral Pledget for Tip Deflection," filed Nov. 29, 2012, issued as U.S. Pat. No. 9,289,207 on Mar. 22, 2016, the disclosure of which is incorporated by reference herein. Various suitable ways in which such teachings may be combined will be apparent to those of ordinary skill in the art.

Similarly, at least some of the teachings herein may be readily combined with one or more teachings of U.S. patent application Ser. No. 13/706,827, entitled "Surgical Stapler with Varying Staple Widths Along Different Circumferences," filed Dec. 6, 2012, now abandoned, the disclosure of which is incorporated by reference herein. Various suitable ways in which such teachings may be combined will be apparent to those of ordinary skill in the art.

Similarly, at least some of the teachings herein may be readily combined with one or more teachings of U.S. patent application Ser. No. 13/688,992, entitled "Pivoting Anvil for Surgical Circular Stapler," filed Nov. 29, 2012, issued as U.S. Pat. No. 9,498,222 on Nov. 22, 2016, the disclosure of which is incorporated by reference herein. Various suitable ways in which such teachings may be combined will be apparent to those of ordinary skill in the art.

Similarly, at least some of the teachings herein may be readily combined with one or more teachings of U.S. patent application Ser. No. 13/693,455, entitled "Circular Anvil Introduction System with Alignment Feature," filed Dec. 4, 2012, issued as U.S. Pat. No. 9,724,100 on Aug. 8, 2017, the disclosure of which is incorporated by reference herein. Various suitable ways in which such teachings may be combined will be apparent to those of ordinary skill in the art.

Similarly, at least some of the teachings herein may be readily combined with one or more teachings of U.S. patent application Ser. No. 13/716,308, entitled "Circular Stapler with Selectable Motorized and Manual Control," filed on Dec. 17, 2012 (published as U.S. Pub. No 2014/0166727 on Jun. 19, 2014), issued as U.S. Pat. No. 9,445,816 on Sep. 20, 2016, the disclosure of which is incorporated by reference herein. Various suitable ways in which such teachings may be combined will be apparent to those of ordinary skill in the art.

Similarly, at least some of the teachings herein may be readily combined with one or more teachings of U.S. patent application Ser. No. 13/716,318, entitled "Motor Driven Rotary Input Circular Stapler with Modular End Effector," filed on Dec. 17, 2012 (published as U.S. Pub. No. 2014/0166728 on Jun. 19, 2014), issued as U.S. Pat. No. 9,597,081 on Mar. 21, 2017, the disclosure of which is incorporated by reference herein. Various suitable ways in which such teachings may be combined will be apparent to those of ordinary skill in the art.

As described in U.S. patent application Ser. No. 13/716,318, issued as U.S. Pat. No. 9,597,081 on Mar. 21, 2017, FIGS. 21-28 show various features that are used to drive stapling head assembly (440) of the present example. In particular, these features include a first rotary drive element (450), a second rotary drive element (460), a drive nut (470), and a clamping driver (480). These components (450, 460, 470, 480) are coaxially aligned with drive shaft (432) and are all housed within a cartridge housing (600), which will be described in greater detail below. As can also be seen in FIG. 21, stapling head assembly (440) includes staple deck (442), a staple driver (443), and a cylindraceous knife (445). Staple driver (443) is operable to translate distally to drive staples (not shown) through openings in staple deck (442) and into staple forming pockets of proximal face (496) of anvil (490). Knife (445) translates distally with staple driver (443), thereby cutting tissue at substantially the same time that the adjacent tissue is being stapled.

Figure 22:
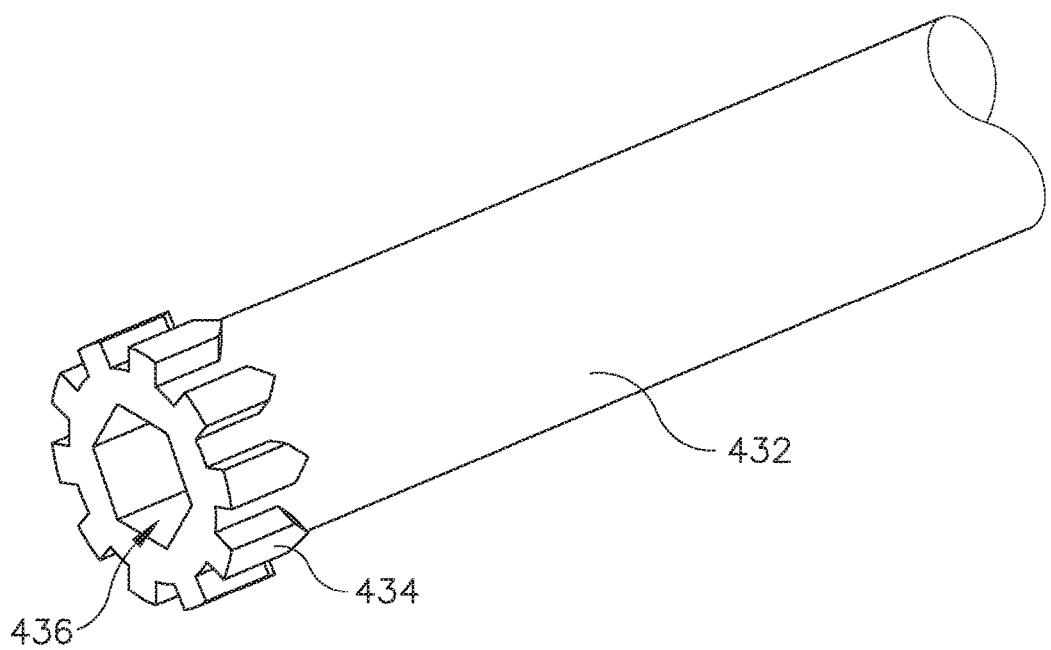
FIG. 22 depicts a partial perspective view of the distal end of the rotary drive shaft of the surgical instrument of FIG. 21.
Figure 23:
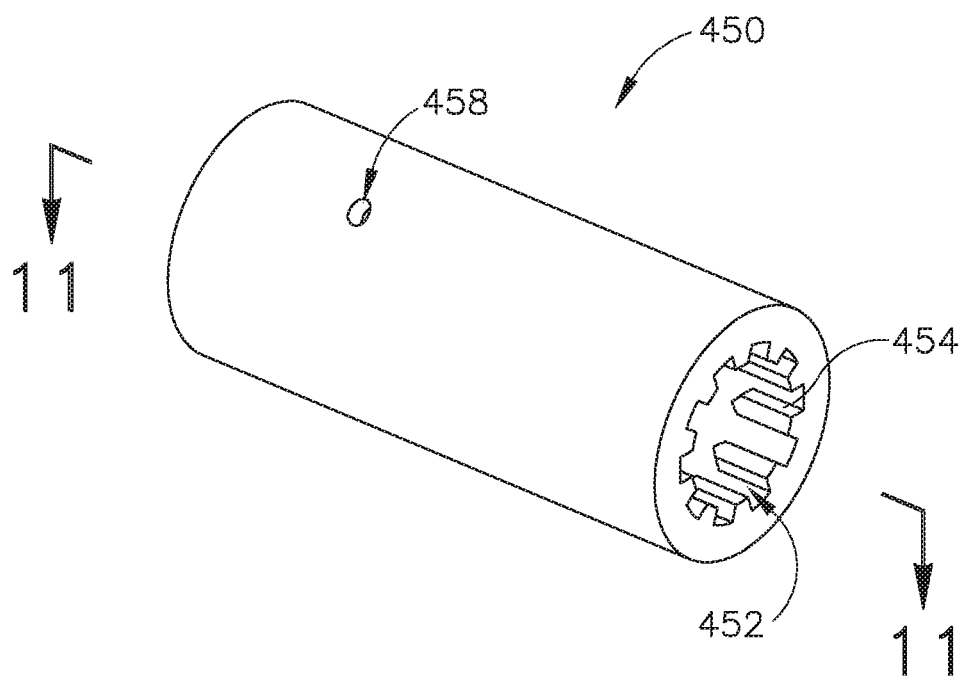
FIG. 23 depicts a perspective view of a first rotary drive element of the stapling head assembly of FIG. 21.
Figure 24:
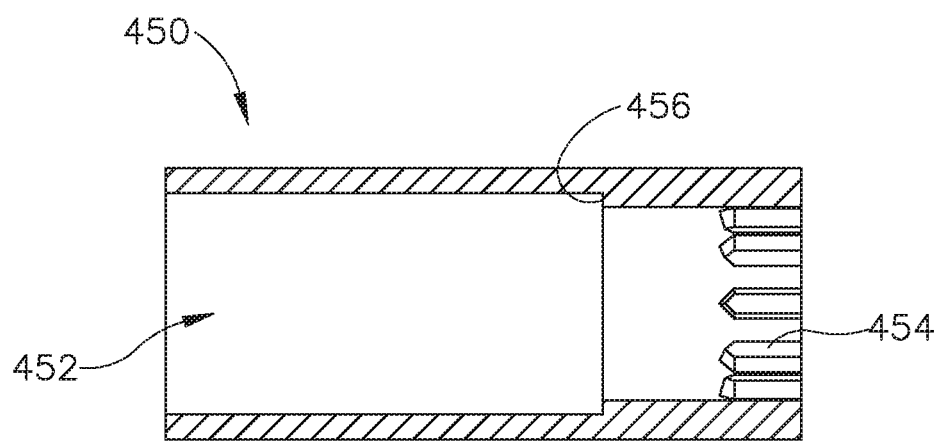
FIG. 24 depicts a cross-sectional view of the first rotary drive element of FIG. 23, taken along line 11-11 of FIG. 23.

As best seen in FIGS. 23-24, first rotary drive element (450) defines a bore (452) and includes a proximal set of inner splines (454). The diameter of bore (452) increases distal to inner splines (454), such that first rotary drive element (450) includes a distally facing annular shoulder (456). First rotary drive element (450) also includes a threaded opening (458) that extends transversely from the exterior of first rotary drive element (450) into bore (452). As shown in FIG. 22, the distal end of drive shaft (432) includes a set of outer splines (434) that complement inner splines (454) of first rotary drive element (450). Thus, when splines (434, 454) are at a common longitudinal position, rotation of drive shaft (432) rotates first rotary drive element (450). In the present example, splines (434, 454) are at a common longitudinal position when drive shaft (432) is in a proximal position. When drive shaft (432) is driven to a distal position (e.g., by sliding control ring (416) distally), splines (434, 435) disengage such that rotation of drive shaft (432) will not rotate first rotary drive element (450). As shown in FIGS. 22-24, splines (434, 454) have complementary tapered ends to promote positioning of splines (434) in the interstices between splines (454) when drive shaft (432) is translated back from the distal position to the proximal position.

Figure 25:
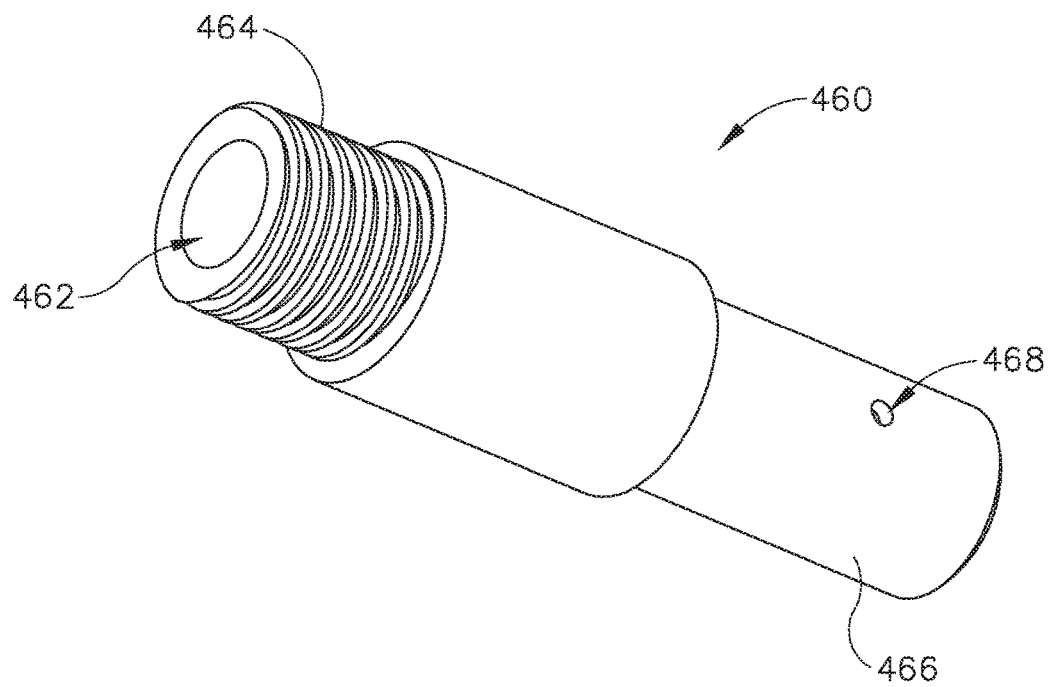
FIG. 25 depicts a perspective view of a second rotary drive element of the stapling head assembly of FIG. 21.

As best seen in FIG. 25, second rotary drive element (460) of the present example defines an inner bore (462), includes outer threading (464) at its distal end, and includes a necked-down proximal portion (466). A threaded opening (468) extends transversely from the exterior of second rotary drive element (460) into bore (462). Proximal portion (466) is configured to slidably fit within bore (462) of first rotary drive element (450). In particular, threaded openings (458, 468) align with each other when proximal portion (466) is disposed in bore (452), and a set screw is secured in threaded openings (458, 468) to secure first and second rotary drive elements (450, 460) together. First and second rotary drive elements (450, 460) will thus rotate together unitarily.

Figure 21:
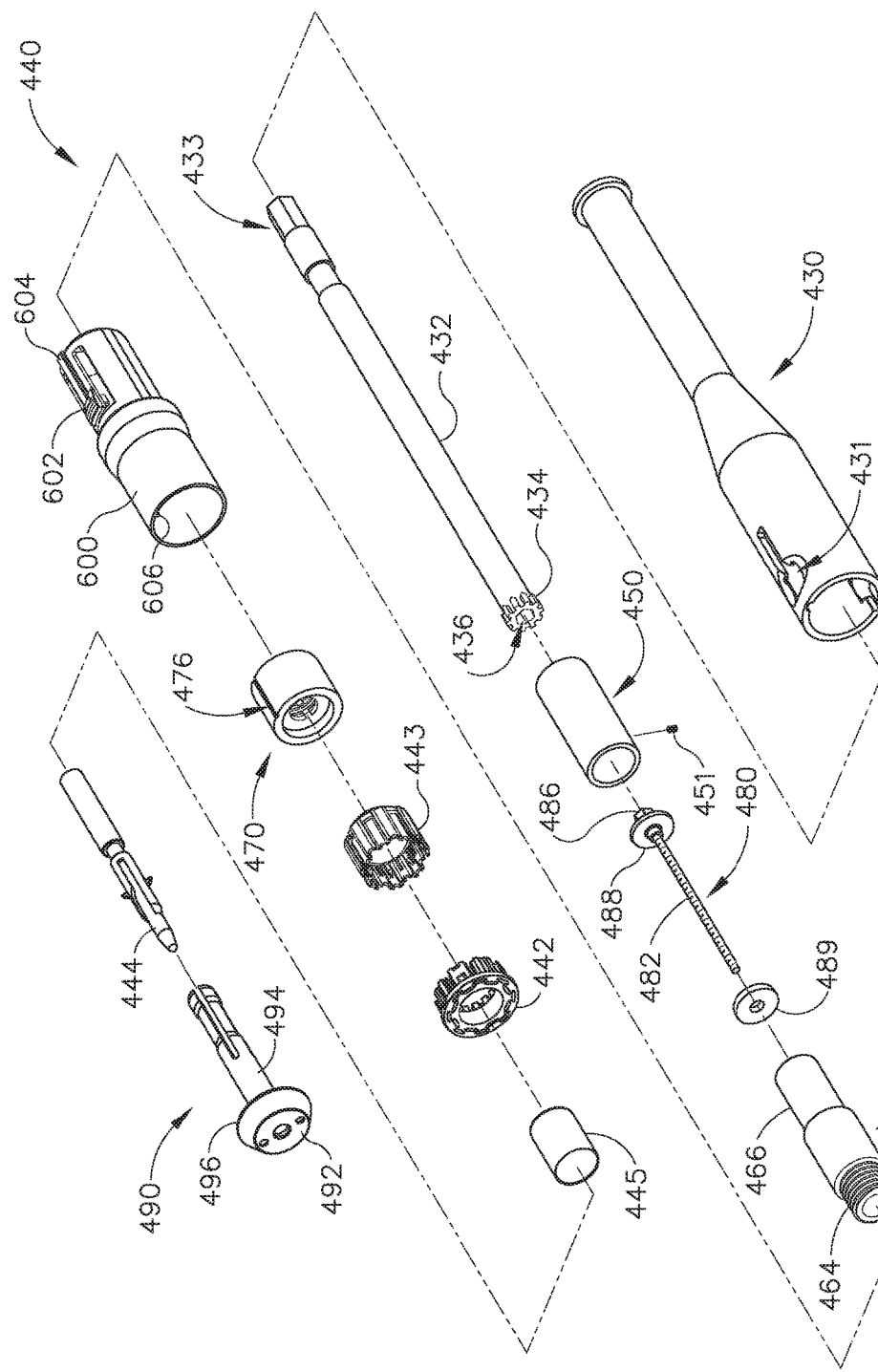
FIG. 21 depicts a partially exploded view of a surgical instrument, showing components of a stapling head assembly.
Figure 26:
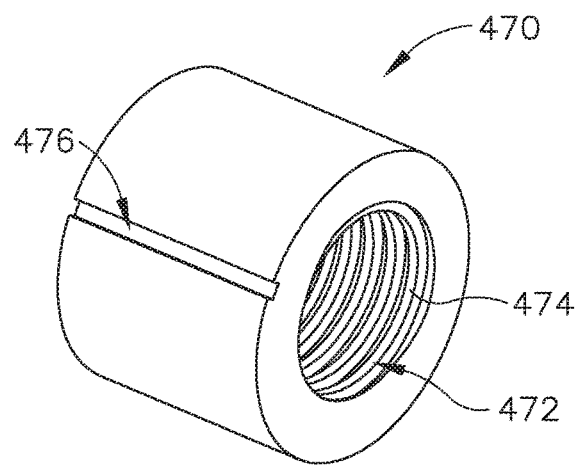
FIG. 26 depicts a perspective view of a drive nut of the stapling head assembly of FIG. 21.

As best seen in FIG. 26, drive nut (470) of the present example defines an inner bore (472), includes an inner threading (474), and includes an outer keyway (476). Bore (472) is configured to receive the distal end of second rotary drive element (460). In particular, threading (464) meshes with threading (474). Outer keyway (476) receives a key (606) that extends inwardly from cartridge housing (600) (as shown in FIG. 21). The relationship between keyway (476) and key (606) prevents drive nut (470) from rotating relative to cartridge housing (600); but permits drive nut (470) to translate relative to cartridge housing (600). It should therefore be understood that, when drive shaft (432) and rotary drive elements (450, 460) rotate together, the relationship between threading (464, 474) will cause drive nut (470) to translate distally or proximally within cartridge housing (600), depending on the direction in which drive shaft (432) and rotary drive elements (450, 460) are rotated. Staple driver (443) and knife (445) are fixedly secured to drive nut (470) in this example, such that staple driver (443) and knife (445) translate unitarily with drive nut (470) relative to staple deck (442) and relative to cartridge housing (600). It should therefore be understood that, when drive shaft (432) is at a proximal position and is rotated, such rotation will drive staple driver (443) and knife (445) distally or proximally relative to staple deck (442) and relative to cartridge housing (600), depending on the direction of rotation.

Figure 27:
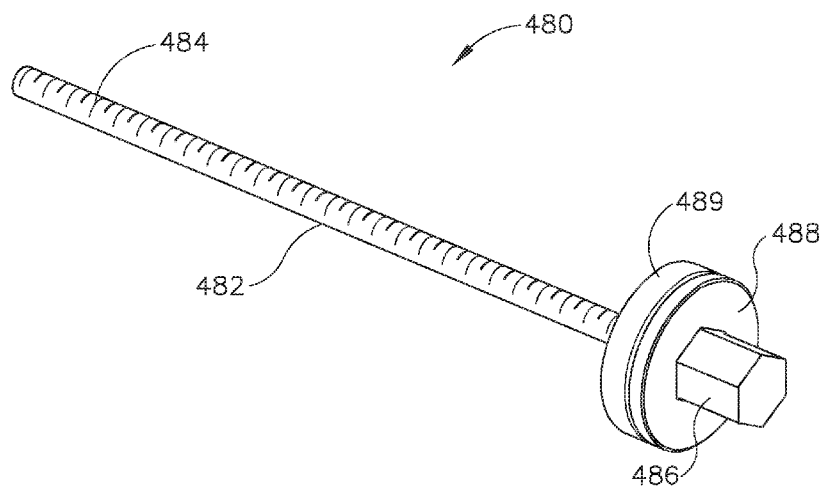
FIG. 27 depicts a perspective view of a clamping driver of the stapling head assembly of FIG. 21.
Figure 28:
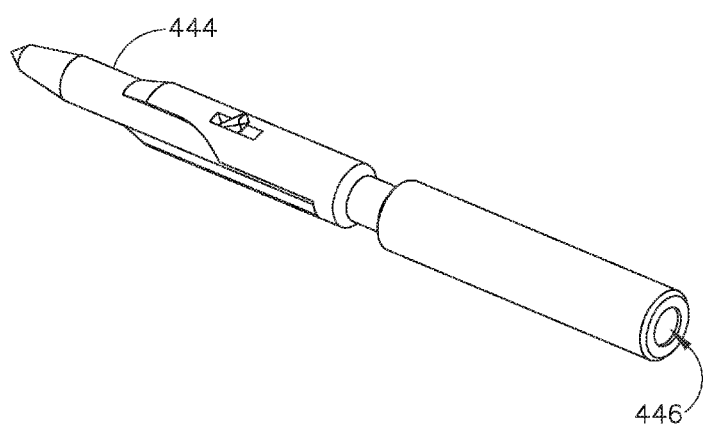
FIG. 28 depicts a perspective view of the trocar of the stapling head assembly of FIG. 21.

As best seen in FIG. 27, clamping driver (480) of the present example comprises a shaft (482) with threading (484) at the distal end of shaft (482). Clamping driver (480) also includes a proximal drive feature (486), an annular flange (488), and a thrust bearing (489) that is positioned about shaft (482) and distal to annular flange (488). As best seen in FIGS. 29A-29D, shaft (482) extends longitudinally through bores (452, 462, 472) to reach trocar (444). As best seen in FIG. 28, the proximal end of trocar (444) includes a threaded opening (446). Threaded opening (446) is configured to receive the distal end of shaft (482), thereby meshing with threading (484). Trocar (444) is operable to translate relative to cartridge housing (600) but not rotate relative to cartridge housing (600). Thus, trocar (444) will translate relative to cartridge housing (600) in response to rotation of clamping driver (480) relative to cartridge housing (600), due to interaction between threading (484) and threaded opening (446). As can also be seen in FIGS. 29A-29D, flange (488) and thrust bearing (489) are captured between shoulder (456) of first rotary drive element (450) and the proximal end (466) of second rotary drive element (460), such that rotary drive elements (450, 460) prevent clamping driver (480) from moving longitudinally.

Proximal drive feature (486) has a hexagonal cross-section in this example, and is thus configured to complement a hexagonal recess (436) formed at the distal end of drive shaft (432) as shown in FIG. 22. While hexagonal shapes are used in the present example, it should be understood that any other suitable shape may be used, including but not limited to rectangular, semicircular, triangular, elliptical, etc. When drive shaft (432) is at the distal position (e.g., when control ring (416) is in the distal position), proximal drive feature (486) is received in hexagonal recess (436), such that rotation of drive shaft (432) rotates clamping driver (480). When drive shaft (432) is at the proximal position (e.g., when control ring (416) is in the proximal position), proximal drive feature (486) is disengaged from hexagonal recess (436), such that rotation of drive shaft (432) does not rotate clamping driver (480).

It should be understood from the foregoing that, when drive shaft (432) is at the distal position, rotation of drive shaft (432) will rotate clamping driver (480) but not rotary drive elements (450, 460). When drive shaft (432) is in the proximal position, rotation of drive shaft (432) will rotate rotary drive elements (450, 460) but not clamping driver (480). Thus, drive shaft (432) may be rotated and translated in a particular sequence to provide clamping, cutting, and stapling of tissue. An example of such a sequence is shown in FIGS. 29A-29D.

Figure 29A:
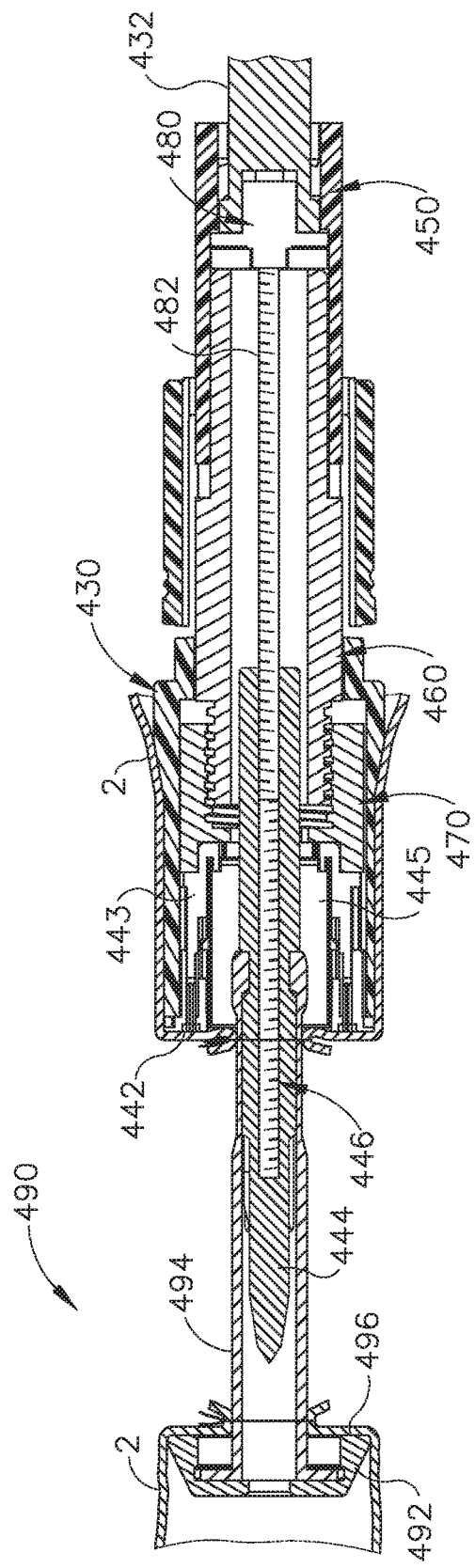
FIG. 29A depicts a cross-sectional side view of the stapling head assembly of FIG. 21, with the anvil in an open position and with the rotary drive shaft in a distal position.

In particular, FIG. 29A shows anvil (490) coupled with trocar (444) and drive shaft (432) in the distal position. It should be understood that control ring (416) is also in the distal position at this stage. Head (492) of anvil (490) is positioned in a first lumen defined by tissue (2), with shaft (494) of anvil (490) protruding from lumen. A suture is used to secure tissue (2) about shaft (494) in a purse-string fashion. In some uses, tissue (2) defines an upper section of a gastrointestinal tract, such as an upper colon portion or an upper esophagus portion. It should be understood that anvil (490) may travel proximally through lumen before being coupled with trocar (444). Stapling head assembly (440) is positioned within a second lumen defined by tissue (2). A suture is used to secure tissue (2) about trocar (444) in a purse-string fashion. In some uses, tissue (2) defines a lower section of a gastrointestinal tract, such as a lower colon portion or a lower esophagus portion. It should be understood that stapling head assembly (440) may travel distally through lumen before being coupled with anvil (490).

Figure 29B:
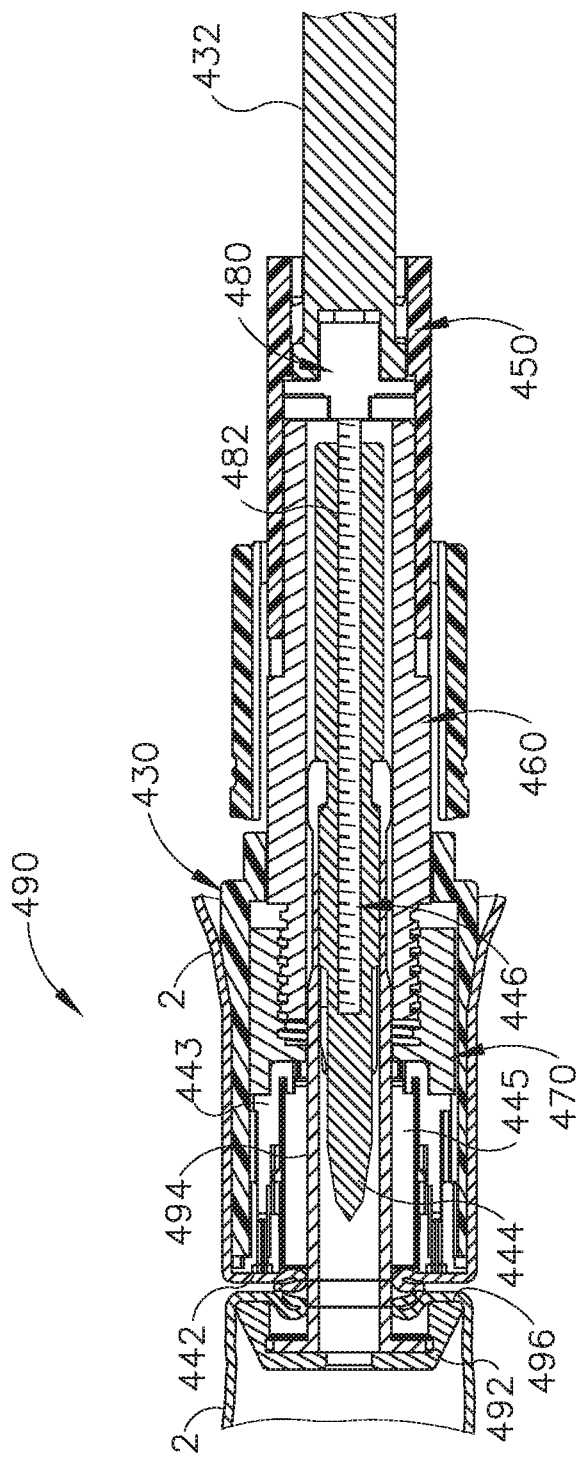
FIG. 29B depicts a cross-sectional side view of the stapling head assembly of FIG. 21, with the anvil in a closed position and with the rotary drive shaft in the distal position.

With anvil (490) and stapling head assembly (440) coupled and positioned within respective lumens, motor (422) may be activated to rotate drive shaft (432). If handle assembly (410) is in manual operation mode, control knob (414) may be manually rotated to rotate drive shaft (432). With drive shaft (432) being in the distal position, drive feature (486) of clamping driver (480) is seated in recess (436) of drive shaft (432), such that rotation of drive shaft (432) rotates clamping driver (480). This rotation retracts trocar (444) and anvil (490) proximally relative to stapling head assembly (440) as shown in FIG. 29B. This retraction provides clamping of tissue (2) between proximal face (496) of anvil head (492) and staple deck (442). Drive shaft (432) may be rotated until the desired gap between proximal face (496) and staple deck (442) is achieved. The gap may be indicated to the user in numerous ways. By way of example only, stapling instrument (400) may include an equivalent of indicator window as described above. As another merely illustrative example, an encoder or other feature may track rotation of drive shaft (432) and a control module may read such data and accordingly drive an LED display or other type of electronic display to indicate the gap distance to the user. Other suitable ways in which an operator may receive gap distance feedback will be apparent to those of ordinary skill in the art in view of the teachings herein.

Figure 29C:
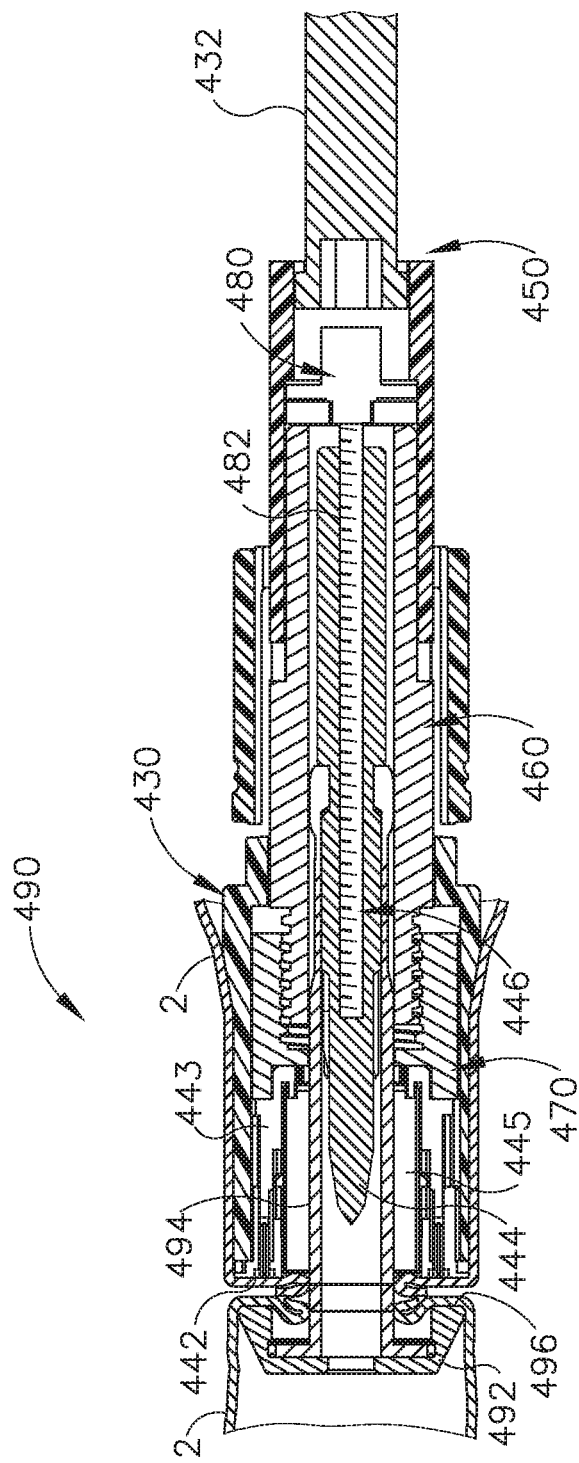
FIG. 29C depicts a cross-sectional side view of the stapling head assembly of FIG. 21, with the anvil in the closed position and with the rotary drive shaft shifted to a proximal position.

Once the operator has achieved the desired gap between proximal face (496) and staple deck (442), the user may translate drive shaft (432) proximally as shown in FIG. 29C. This may be done by translating control ring (416) proximally or in any other suitable fashion. When drive shaft (432) translates proximally (432), recess (436) disengages drive feature (486) and splines (434) engage splines (454). The translation of drive shaft (432) from the distal position to the proximal position thus shifts stapling head assembly (440) from a tissue clamping mode to a tissue cutting/stapling mode. In some other versions, stapling head assembly (440) is configured such that translating drive shaft from the distal position to the proximal position shifts stapling head assembly (440) from a tissue cutting/stapling mode to a tissue clamping mode; and vice-versa.

Figure 29D:
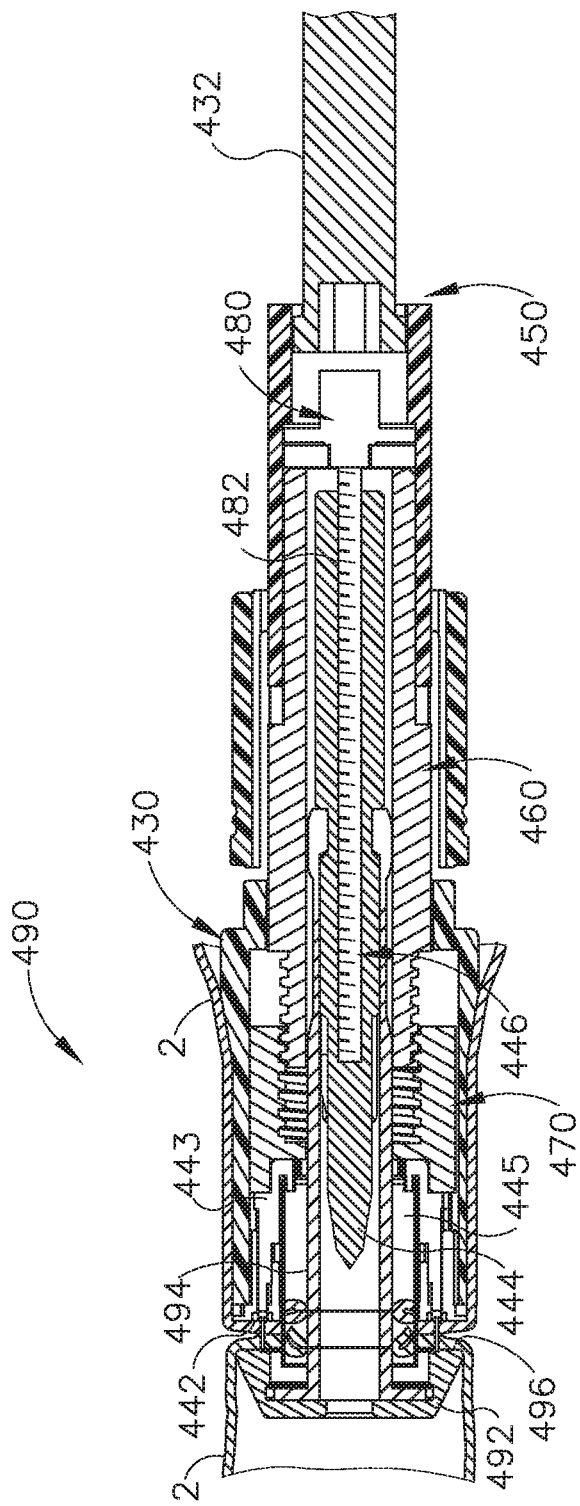
FIG. 29D depicts a cross-sectional side view of the stapling head assembly of FIG. 21, with the staple driver and blade in a fired position.

Once stapling head assembly (440) is shifted from tissue clamping mode to tissue cutting/stapling mode, drive shaft (432) may again be rotated. Again, this may be accomplished by activating motor (422); or by rotating control knob (414) manually if handle assembly (410) is in manual operation mode. In some instances, an operator may prefer to use handle assembly (410) in manual operation mode during tissue clamping (FIGS. 29A-29B), and then use handle assembly (410) in motorized mode during tissue cutting/stapling (FIGS. 29C-29D); or vice versa. In either case, when drive shaft (432) is rotated during tissue cutting/stapling mode, this rotation is communicated through rotary drive elements (450, 460). The rotation of rotary drive elements (450, 460) drives drive nut (470) distally as shown in FIG. 29D, due to engagement between threading (464, 474). This distal advancement of drive nut (470) advances staple driver (443), and knife (445) distally, thereby cutting and stapling tissue (2). An encoder, force sensor, timer, and/or any other suitable feature may be used determine when to stop motor (422) automatically upon sufficient advancement of drive nut (470), staple driver (443), and knife (445).

After tissue (2) has been stapled and cut, drive shaft (432) may be advanced distally again to engage clamping driver (480), then rotated in the opposite direction to drive anvil (490) slightly away from stapling head assembly (440). With anvil (490) still coupled with stapling head assembly (440), stapling instrument (400) may then be withdrawn proximally through lumen (2), leaving a secure and fluid tight anastomosis joining lumens together. Other suitable ways in which stapling instrument (400) may be used will be apparent to those of ordinary skill in the art in view of the teachings herein.

Figure 30A:
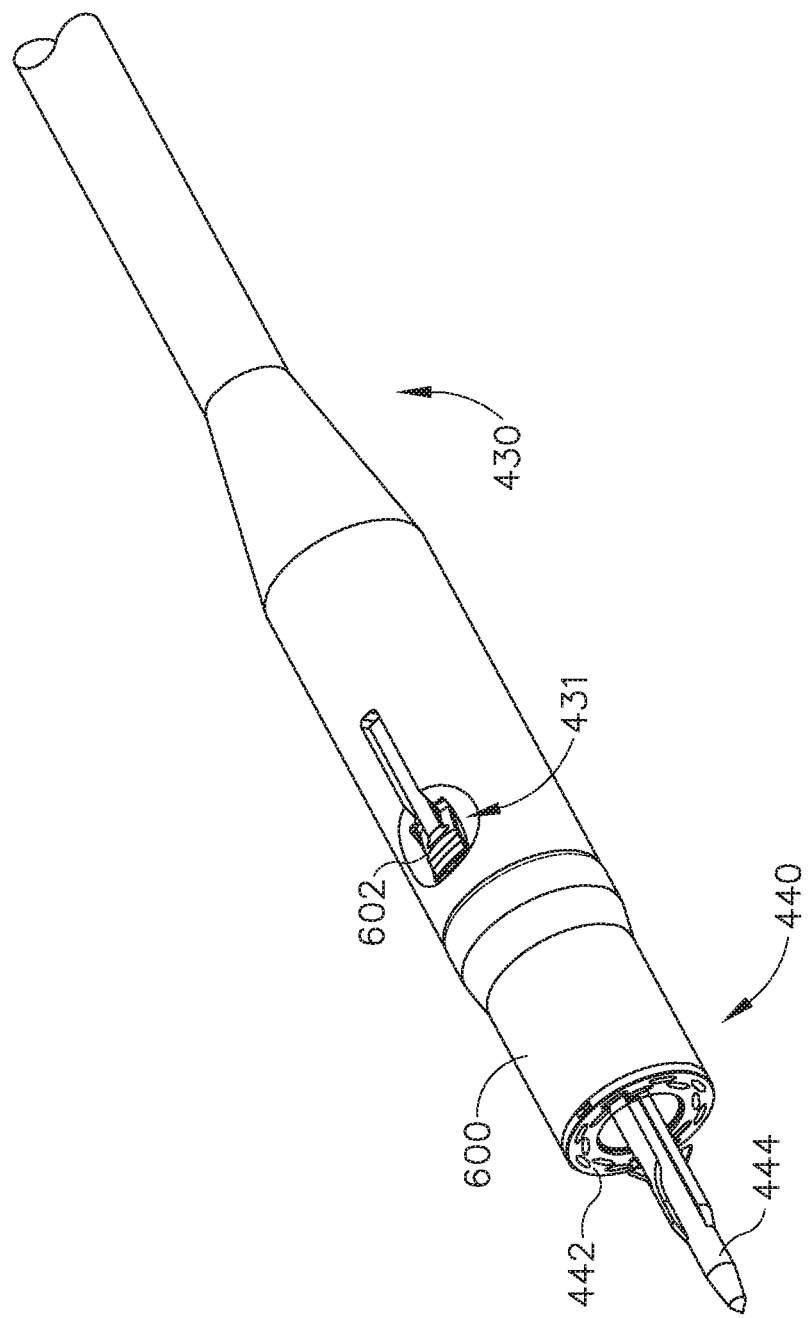
FIG. 30A depicts a perspective view of the stapling head assembly of FIG. 21, with the stapling head cartridge coupled with the shaft assembly.
Figure 30B:
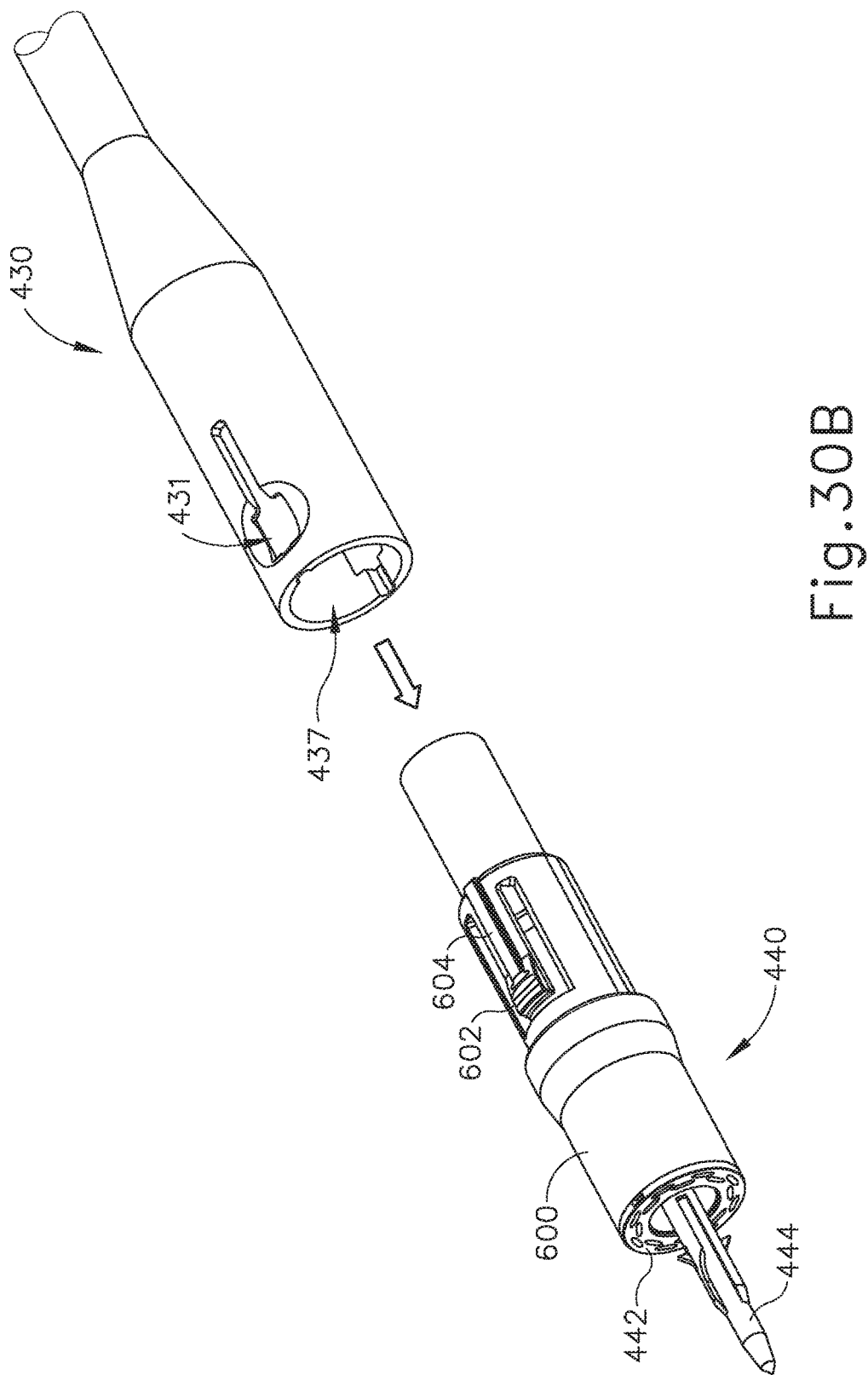
FIG. 30B depicts a perspective view of the stapling head assembly of FIG. 21, with the stapling head cartridge decoupled from the shaft assembly.
Figure 31:
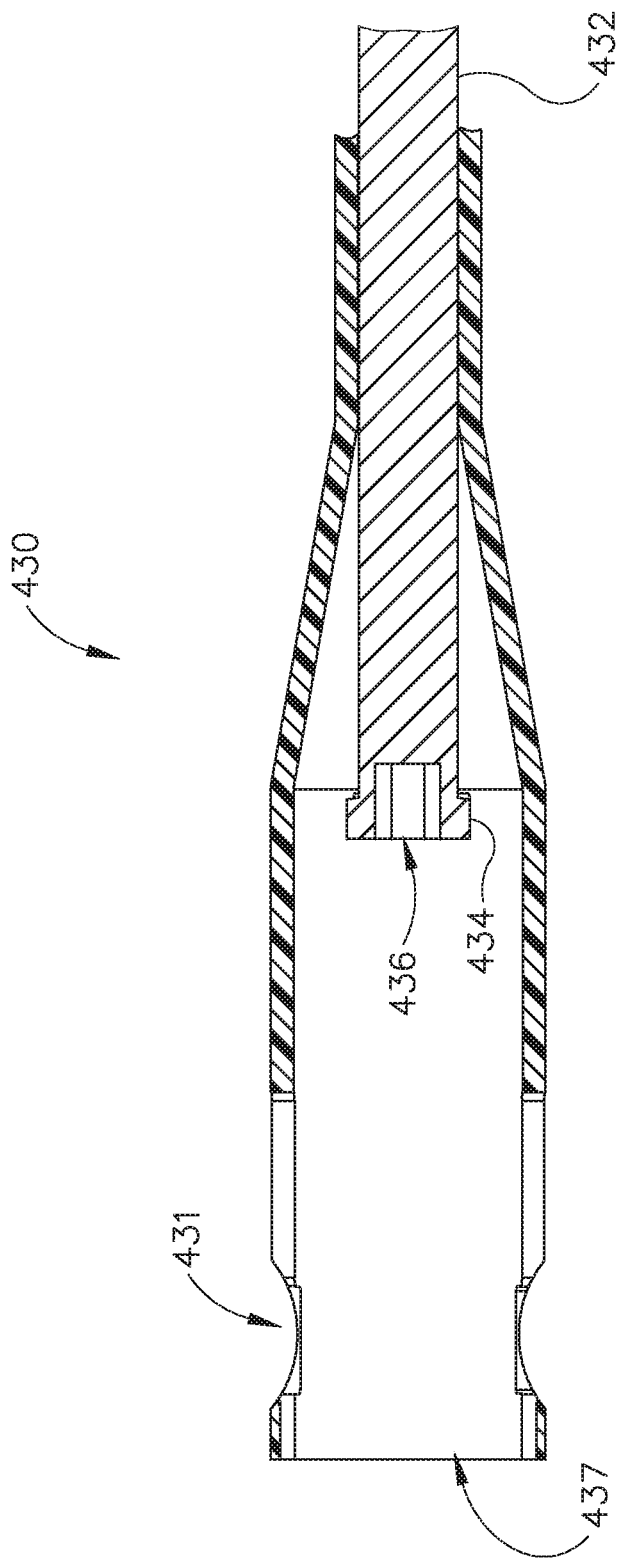
FIG. 31 depicts a cross-sectional view of the distal end of the shaft assembly of the surgical instrument of FIG. 21.

In some instances, it may be desirable to permit removal of at least part of stapling head assembly (440) from the rest of stapling instrument (400). FIGS. 30A-31 show exemplary features that are incorporated into stapling head assembly (440) and shaft assembly (430) of the present example to enable removal of stapling head assembly (440) from shaft assembly (430). In particular, FIGS. 30A-31 show stapling head assembly (440) being provided in a cartridge housing (600) that is removable from the distal end of shaft assembly (430). Cartridge housing (600) includes a pair of outwardly extending tabs (602) that are positioned at the free ends of respective resilient arms (604). The distal end of shaft assembly (430) presents a socket (437) that receives cartridge housing (600). Socket (437) includes a pair of lateral openings (431) that correspond with tabs (602) of cartridge housing (602). In particular, resilient arms (604) are configured to resiliently bias tabs (602) into openings (431) when cartridge housing (600) is fully seated in socket (437), thereby locking cartridge housing (600) in place relative to shaft assembly (430). As best shown in FIG. 31, the distal end of drive shaft (432) is positioned within socket (437), such that the distal end of drive shaft (432) will enter bore (452) of first rotary drive element (450) when cartridge housing (600) is fully seated in socket (437).

In order to remove cartridge housing (600) from socket (437), and thereby decouple stapling head assembly (440) from shaft assembly (430), a user may depress both tabs (602) inwardly to decouple tabs (602) from openings (431). While holding tabs (602) in these depressed positions, the user may then pull cartridge housing (600) distally away from shaft assembly (430) as shown in the transition from FIG. 20A to FIG. 30B. At some point thereafter, another cartridge housing (600) may be inserted into socket (437). In some instances, this may be performed during a single surgical procedure. For instance, if the operator made a mistake during an initial attempt at securing an anastomosis and failed to properly deploy staples from stapling head assembly (440), the operator may withdraw stapling head assembly from the surgical site and re-load shaft assembly (430) with another stapling head assembly (440) to try completing the anastomosis again with the same stapling instrument (400). The operator would thus avoid the need to dispose of the entire stapling instrument (400) and use a completely new stapling instrument (400).

As another merely illustrative example, stapling instrument (400) may be provided as a partially reusable device. For instance, after being used in a surgical procedure, a nurse or other personnel may remove stapling head assembly (440) from shaft assembly (430) and dispose of the used stapling head assembly (440). The rest of stapling instrument (400) may then be sent to a sterilization process or other reclamation process. In instances where stapling instrument (400) includes a power source (420), motor (422), and/or other electronic components, such components may be removed for separate processing while the remainder of shaft assembly (430) and handle assembly (410) are sterilized in any suitable fashion. After processing, the previously used shaft assembly (430) and handle assembly (410) may be combined with a new stapling head assembly (440) for use in another surgical procedure. Various other suitable ways in which components of stapling instrument (400) may be handle before, during, and after surgical procedures will be apparent to those of ordinary skill in the art in view of the teachings herein.

Of course, the modular cartridge configuration of stapling head assembly (440) in the present example is merely optional. Other suitable ways in which at least part of stapling head assembly (440) may be provided in a cartridge or modular form will be apparent to those of ordinary skill in the art in view of the teachings herein. It should also be understood that some versions of stapling head assembly (440) may simply be unitary with shaft assembly (430), such that stapling head assembly (440) may not be removed from shaft assembly (430). By way of example only, some such versions of stapling instrument (400) may be configured for a single use only, such that the entire stapling instrument (400), including stapling head assembly (440), is disposed of after a single use. Other suitable variations will be apparent to those of ordinary skill in the art in view of the teachings herein.

Similarly, at least some of the teachings herein may be readily combined with one or more teachings of U.S. patent application Ser. No. 13/716,323, entitled "Motor Driven Rotary Input Circular Stapler with Lockable Flexible Shaft," filed Dec. 17, 2012 (published as U.S. Pub. No. 2014/0166718 on Jun. 19, 2014), issued as U.S. Pat. No. 9,463,022 on Oct. 11, 2016, the disclosure of which is incorporated by reference herein. Various suitable ways in which such teachings may be combined will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art.

For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. A surgical instrument, comprising:
  (a) a stapling head assembly, wherein at least a portion of the stapling head assembly is configured to removably couple with a portion of a shaft assembly, the stapling head assembly including:
    (i) a cartridge housing surrounding and extending along a longitudinal axis from a distal end portion to a proximal end portion thereof,
    (ii) a staple deck positioned within the distal end portion of the cartridge housing, wherein the staple deck includes an annular array of staple pockets positioned about the longitudinal axis,
    (iii) a plurality of staples positioned respectively within the annular array of staple pockets,
    (iv) a staple driver positioned proximally from the plurality of staples within the cartridge housing and configured to translate distally from a proximal driver position toward a distal driver position to thereby drive each of the plurality of staples distally from the annular array of staple pockets, respectively, for forming the plurality of staples in a tissue of a patient,
    (v) a cylindraceous knife surrounding the longitudinal axis and positioned radially inward from the annular array of staple pockets within the cartridge housing, wherein the cylindraceous knife is configured to translate distally from a proximal knife position toward a distal knife position for cutting the tissue of the patient,
    (vi) a trocar extending distally along the longitudinal axis, wherein the trocar is configured to couple with an anvil for forming the plurality of staples thereagainst, and wherein the trocar is further configured to translate longitudinally between a proximal trocar position and a distal trocar position for positioning the anvil longitudinally relative to the staple deck,
    (vii) a first drive member configured to receive a rotatable drive element thereagainst, wherein the first drive member is configured to drive translation of at least one of the staple driver, the cylindraceous knife, or the trocar in response to rotation of the rotatable drive element in a first direction, and
    (viii) a second drive member configured to receive the rotatable drive element thereagainst, wherein the second drive member is configured to drive translation of a remaining of the at least one of the staple driver, the cylindraceous knife, or the trocar in response to rotation of the rotatable drive element in the first direction, wherein the second drive member is positioned radially inwardly from the first drive member, and
    wherein each of the first and second drive members is coaxial with the longitudinal axis.
2. The surgical instrument of claim 1, wherein the cylindraceous knife extends coaxially along the longitudinal axis.
3. The surgical instrument of claim 2, wherein the cartridge housing, the staple deck, and the staple driver extend coaxially along the longitudinal axis.

4. The surgical instrument of claim 1, further comprising a first locking feature operatively connected to the cartridge housing and positioned proximally from the staple deck, wherein the first locking feature is configured to be removably coupled against the portion of the shaft assembly for selectively coupling and decoupling the stapling head assembly relative to the portion of the shaft assembly.
5. The surgical instrument of claim 4, wherein the first locking feature is selected from the group consisting of: an opening and a tab.
6. The surgical instrument of claim 4, further comprising a shaft assembly having a distal end portion, wherein the distal end portion of the shaft assembly is configured to removably couple with the stapling head assembly.
7. The surgical instrument of claim 6, wherein the distal end portion of the shaft assembly includes a second locking feature configured to be removably coupled against the stapling head assembly for selectively coupling and decoupling the stapling head assembly relative to the distal end portion of the shaft assembly.
8. The surgical instrument of claim 7, wherein at least one of the first or second locking features is an opening configured to receive a tab for removably coupling the stapling head assembly to the distal end portion of the shaft assembly.
9. The surgical instrument of claim 1, wherein the first drive member surrounds and extends along the longitudinal axis, and wherein the second drive member is positioned on the longitudinal axis.
10. The surgical instrument of claim 9, wherein the first drive member includes a first threading, wherein the second drive member includes a second threading.
11. The surgical instrument of claim 9, wherein the first drive member is configured to drive translation of at least one of the staple driver or the cylindraceous knife in response to rotation of the rotatable drive element in the first direction, wherein the second drive member is configured to drive translation of the trocar in response to rotation of the rotatable drive element in the first direction.
12. The surgical instrument of claim 11, wherein the first drive member is configured to simultaneously drive translation of each of the staple driver and the cylindraceous knife in response to rotation of the rotatable drive element.
13. The surgical instrument of claim 9, wherein the first drive member includes a bore extending along the longitudinal axis, wherein the second drive member includes a shaft extending along the longitudinal axis, and wherein the bore of the first drive member receives the shaft of the second drive member.
14. The surgical instrument of claim 1, wherein the staple driver is configured to translate proximally from the distal driver position toward the proximal driver position, wherein the cylindraceous knife is configured to translate proximally from the distal knife position toward the proximal knife position, wherein at least one of the first r second drive members is configured to drive proximal translation of at least one of the staple driver or the cylindraceous knife in response to rotation of the rotatable drive element in a second direction.
15. The surgical instrument of claim 14, wherein the second direction of rotation is opposite the first direction of rotation.
16. The surgical instrument of claim 1, wherein the stapling head assembly further includes an anvil releasably coupled with the trocar, wherein the anvil is configured to receive the plurality of staples thereagainst for forming the plurality of staples.

17. The surgical instrument of claim 1, further comprising a body assembly including:
(i) a battery,
(ii) a motor, and
(iii) a drive shaft,
wherein each of the battery, the motor and the drive shaft are operatively connected such that powering the motor with the battery is configured to rotate the drive shaft, wherein the drive shaft is configured to operatively connect to at least one of the first or second drive members for selectively driving translation of at least one of the staple driver, the cylindraceous knife, or the trocar.

18. The surgical instrument of claim 17, wherein the drive shaft is selectively movable between a proximal longitudinal position and a distal longitudinal position, wherein the drive shaft in the proximal longitudinal position is configured to operatively connect to one of the first or second drive members for driving rotation thereof, and wherein the drive shaft in the distal longitudinal position is configured to operatively connect to the other of the first or second drive members for driving rotation thereof.

19. A surgical instrument, comprising:
(a) a stapling head assembly, including:
(i) a cartridge housing surrounding and extending along a longitudinal axis from a distal end portion to a proximal end portion thereof,
(ii) a staple deck positioned within the distal end portion of the cartridge housing, wherein the staple deck includes an annular array of staple pockets positioned about the longitudinal axis,
(iii) a plurality of staples positioned respectively within the annular array of staple pockets,
(iv) a staple driver positioned proximally from the plurality of staples within the cartridge housing and configured to translate distally from a proximal driver position toward a distal driver position to thereby drive each of the plurality of staples distally from the annular array of staple pockets, respectively, for forming the plurality of staples in a tissue of a patient,
(v) a cylindraceous knife surrounding the longitudinal axis and positioned radially inward from the annular array of staple pockets within the cartridge housing, wherein the cylindraceous knife is configured to translate distally from a proximal knife position toward a distal knife position for cutting the tissue of the patient,
(vi) a trocar extending distally along the longitudinal axis, wherein the trocar is configured to couple with an anvil for forming the plurality of staples thereagainst, and wherein the trocar is further configured to translate longitudinally between a proximal trocar position and a distal trocar position for positioning the anvil longitudinally relative to the staple deck,
(vii) a first drive member configured to receive a rotatable drive element thereagainst, wherein the first drive member is configured to drive translation of the staple driver and the cylindraceous knife in response to rotation of the rotatable drive element in a first direction, wherein the first drive member surrounds and extends along the longitudinal axis, and
(viii) a second drive member configured to receive the rotatable drive element thereagainst, wherein the second drive member is configured to drive translation of the trocar in response to rotation of the rotatable drive element in the first direction, wherein the second drive member is positioned radially inwardly from the first drive member on the longitudinal axis,
wherein each of the cartridge housing, the staple deck, the staple driver, the first drive member, and the second drive member are coaxial with the longitudinal axis;
(b) a shaft assembly having a distal end portion configured to removably couple with the stapling head assembly; and
(c) a locking feature operatively connected to the cartridge housing and positioned proximally from the staple deck, wherein the locking feature is configured to be removably coupled against the portion of the shaft assembly for selectively coupling and decoupling the stapling head assembly relative to the portion of the shaft assembly, and wherein the locking feature is selected from the group consisting of: an opening and a tab.

20. A method of operating a surgical instrument, wherein the surgical instrument has a stapling head assembly that includes a cartridge housing, a staple deck, a plurality of staples, a staple driver, a cylindraceous knife, a first drive member configured to receive a rotatable drive element thereagainst, and a second drive member configured to receive a rotatable drive element thereagainst, wherein each of the first and second drive members are configured to direct translation of at least one of the staple driver, the cylindraceous knife, or the trocar upon receiving rotation therefrom, wherein each of the first and second drive members is coaxial with the longitudinal axis wherein the second drive member is positioned radially inward from the first drive member, and wherein each of the first and second drive members is coaxial with the longitudinal axis, the method comprising:
(a) rotating at least one of the first r second drive members about the longitudinal axis thereby longitudinally translating at least one of the staple driver, the cylindraceous knife, or the trocar upon receiving rotation therefrom.

* * * * *